(12) United States Patent
Kehres

(10) Patent No.: US 11,559,403 B2
(45) Date of Patent: Jan. 24, 2023

(54) MODULAR AUGMENT COMPONENT

(71) Applicant: Biomet Manufacturing, LLC, Warsaw, IN (US)

(72) Inventor: Clinton E. Kehres, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 66 days.

(21) Appl. No.: 17/324,555

(22) Filed: May 19, 2021

(65) Prior Publication Data

US 2021/0267763 A1    Sep. 2, 2021

Related U.S. Application Data

(62) Division of application No. 16/475,215, filed as application No. PCT/US2018/013795 on Jan. 16, 2018, now Pat. No. 11,141,276.

(60) Provisional application No. 62/448,547, filed on Jan. 20, 2017.

(51) Int. Cl.
*A61F 2/30* (2006.01)
*A61F 2/40* (2006.01)

(52) U.S. Cl.
CPC ........ *A61F 2/30734* (2013.01); *A61F 2/4081* (2013.01); *A61F 2002/3092* (2013.01); *A61F 2002/30736* (2013.01); *A61F 2002/30881* (2013.01)

(58) Field of Classification Search
CPC ............... A61F 2/4081; A61F 2/30734; A61F 2002/30736
See application file for complete search history.

(56) References Cited

U.S. PATENT DOCUMENTS

| 2,947,308 | A | 8/1960 | Gorman |
| 3,605,123 | A | 9/1971 | Hahn |
| 3,658,056 | A | 4/1972 | Huggler et al. |
| D230,429 | S | 2/1974 | Davidson et al. |
| 3,855,638 | A | 12/1974 | Pilliar |
| 3,871,031 | A | 3/1975 | Boutin |
| 3,891,997 | A | 7/1975 | Herbert |
| 3,903,549 | A | 9/1975 | Deyerle |
| 3,906,550 | A | 9/1975 | Rostoker et al. |
| 3,918,102 | A | 11/1975 | Eichler |

(Continued)

FOREIGN PATENT DOCUMENTS

| AU | 2004203348 A1 | 9/2005 |
| CA | 2473633 A1 | 9/2005 |

(Continued)

OTHER PUBLICATIONS

U.S. Appl. No. 29/369,066, filed Sep. 1, 2010, Prosthetic Implant Support Structure.

(Continued)

*Primary Examiner* — Javier G Blanco
(74) *Attorney, Agent, or Firm* — Schwegman Lundberg & Woessner, P.A.

(57) ABSTRACT

Disclosed is a central augment. The central augment can include a body and a protrusion. The body can include a first curved surface shaped to interface with a central portion of a bone and a second surface opposite the first curved surface and defining a recess sized to receive a portion of a prosthetic component. The protrusion can extend from the second surface within the recess.

20 Claims, 5 Drawing Sheets

(56) References Cited

U.S. PATENT DOCUMENTS

| | | |
|---|---|---|
| 4,064,567 A | 12/1977 | Burstein et al. |
| 4,136,405 A | 1/1979 | Pastrick et al. |
| 4,164,794 A | 8/1979 | Spector et al. |
| 4,206,516 A | 6/1980 | Pilliar |
| 4,216,549 A | 8/1980 | Hillberry et al. |
| 4,219,893 A | 9/1980 | Noiles |
| 4,224,696 A | 9/1980 | Murray et al. |
| 4,404,691 A | 9/1983 | Buning et al. |
| 4,444,061 A | 4/1984 | Mathias |
| 4,523,587 A | 6/1985 | Frey |
| 4,549,319 A | 10/1985 | Meyer |
| 4,550,448 A | 11/1985 | Kenna |
| 4,566,138 A | 1/1986 | Lewis et al. |
| 4,659,331 A | 4/1987 | Matthews et al. |
| 4,662,891 A | 5/1987 | Noiles |
| 4,678,470 A | 7/1987 | Nashef et al. |
| 4,693,721 A | 9/1987 | Ducheyne |
| 4,711,639 A | 12/1987 | Grundei |
| 4,718,909 A | 1/1988 | Brown |
| 4,735,625 A | 4/1988 | Davidson |
| 4,778,473 A | 10/1988 | Matthews et al. |
| 4,789,663 A | 12/1988 | Wallace et al. |
| 4,790,852 A | 12/1988 | Noiles |
| 4,822,366 A | 4/1989 | Bolesky |
| 4,827,919 A | 5/1989 | Barbarito et al. |
| 4,828,565 A | 5/1989 | Duthoit et al. |
| 4,834,759 A | 5/1989 | Spotorno et al. |
| 4,840,632 A | 6/1989 | Kampner |
| 4,865,607 A | 9/1989 | Witzel et al. |
| 4,878,919 A | 11/1989 | Pavlansky et al. |
| 4,883,448 A | 11/1989 | Kobayashi et al. |
| 4,883,488 A | 11/1989 | Bloebaum et al. |
| 4,888,021 A | 12/1989 | Forte et al. |
| 4,936,859 A | 6/1990 | Morscher et al. |
| 4,938,769 A | 7/1990 | Shaw |
| 4,944,757 A | 7/1990 | Martinez et al. |
| 4,950,298 A | 8/1990 | Gustilo et al. |
| 4,960,427 A | 10/1990 | Noiles |
| 4,964,865 A | 10/1990 | Burkhead et al. |
| 4,986,833 A | 1/1991 | Worland |
| 4,988,359 A | 1/1991 | Frey et al. |
| 5,019,103 A | 5/1991 | Van Zile et al. |
| 5,032,134 A | 7/1991 | Lindwer |
| 5,059,196 A | 10/1991 | Coates |
| 5,092,897 A | 3/1992 | Forte |
| 5,108,446 A | 4/1992 | Wagner et al. |
| 5,133,771 A | 7/1992 | Duncan et al. |
| 5,152,797 A | 10/1992 | Luckman et al. |
| 5,156,626 A | 10/1992 | Broderick et al. |
| 5,163,966 A | 11/1992 | Norton et al. |
| 5,176,711 A | 1/1993 | Grimes |
| 5,192,329 A | 3/1993 | Christie et al. |
| 5,197,488 A | 3/1993 | Kovacevic |
| 5,211,664 A | 5/1993 | Tepic et al. |
| 5,222,984 A | 6/1993 | Forte |
| 5,226,915 A | 7/1993 | Bertin |
| 5,246,459 A | 9/1993 | Elias |
| 5,356,414 A | 10/1994 | Cohen et al. |
| 5,356,629 A | 10/1994 | Sander et al. |
| 5,358,527 A | 10/1994 | Forte |
| 5,358,530 A | 10/1994 | Hodorek |
| 5,370,693 A | 12/1994 | Kelman et al. |
| 5,376,123 A | 12/1994 | Klaue et al. |
| 5,387,241 A | 2/1995 | Hayes |
| 5,395,401 A | 3/1995 | Bahler |
| 5,405,394 A | 4/1995 | Davidson |
| 5,413,604 A | 5/1995 | Hodge |
| 5,443,512 A | 8/1995 | Parr et al. |
| 5,462,563 A | 10/1995 | Shearer et al. |
| 5,480,444 A | 1/1996 | Incavo |
| 5,480,445 A | 1/1996 | Burkinshaw |
| 5,489,311 A | 2/1996 | Cipolletti |
| 5,507,830 A | 4/1996 | DeMane et al. |
| 5,510,396 A | 4/1996 | Prewett et al. |
| 5,531,791 A | 7/1996 | Wolfinbarger, Jr. |
| 5,549,685 A | 8/1996 | Hayes |
| 5,571,198 A | 11/1996 | Drucker |
| 5,591,233 A | 1/1997 | Kelman et al. |
| 5,593,448 A | 1/1997 | Dong |
| 5,609,645 A | 3/1997 | Vinciuerra |
| 5,658,338 A | 8/1997 | Tullos et al. |
| 5,658,349 A | 8/1997 | Brooks et al. |
| 5,662,158 A | 9/1997 | Caldarise |
| 5,683,467 A | 11/1997 | Pappas |
| 5,702,447 A | 12/1997 | Walch et al. |
| 5,702,478 A | 12/1997 | Tornier |
| 5,702,483 A | 12/1997 | Kwong |
| 5,734,959 A | 3/1998 | Krebs et al. |
| 5,766,256 A | 6/1998 | Oudard et al. |
| 5,782,925 A | 7/1998 | Collazo et al. |
| 5,782,929 A | 7/1998 | Sederholm |
| 5,788,976 A | 8/1998 | Bradford |
| 5,800,551 A | 9/1998 | Williamson et al. |
| 5,824,103 A | 10/1998 | Williams et al. |
| 5,858,020 A | 1/1999 | Johnson et al. |
| 5,871,548 A | 2/1999 | Sanders et al. |
| 5,879,393 A | 3/1999 | Whiteside et al. |
| 5,910,172 A | 6/1999 | Penenberg |
| 5,931,409 A | 8/1999 | Nulle et al. |
| 5,957,979 A | 9/1999 | Beckman et al. |
| 5,958,314 A | 9/1999 | Draenert |
| 5,972,368 A | 10/1999 | McKay |
| 5,976,148 A | 11/1999 | Charpenet et al. |
| 5,984,968 A | 11/1999 | Park |
| 5,993,716 A | 11/1999 | Draenert |
| 5,997,581 A | 12/1999 | Khalili |
| 6,008,432 A | 12/1999 | Taylor |
| 6,013,080 A | 1/2000 | Khalili |
| 6,039,764 A | 3/2000 | Pottenger et al. |
| 6,042,612 A | 3/2000 | Voydeville |
| 6,053,945 A | 4/2000 | O'Neil et al. |
| 6,074,423 A | 6/2000 | Lawson |
| 6,074,424 A | 6/2000 | Perrone, Jr. et al. |
| 6,080,195 A | 6/2000 | Colleran et al. |
| 6,117,175 A | 9/2000 | Bosredon |
| 6,126,691 A | 10/2000 | Kasra et al. |
| 6,136,029 A | 10/2000 | Johnson et al. |
| 6,139,581 A | 10/2000 | Engh et al. |
| 6,139,584 A | 10/2000 | Ochoa et al. |
| 6,142,998 A | 11/2000 | Smith et al. |
| 6,162,254 A | 12/2000 | Timoteo |
| 6,162,255 A | 12/2000 | Oyola |
| 6,171,342 B1 | 1/2001 | O'Neil et al. |
| 6,228,119 B1 | 5/2001 | Ondrla et al. |
| 6,264,699 B1 | 7/2001 | Noiles et al. |
| 6,290,725 B1 | 9/2001 | Weiss et al. |
| 6,294,187 B1 | 9/2001 | Boyce et al. |
| 6,328,764 B1 | 12/2001 | Mady |
| 6,355,069 B1 | 3/2002 | DeCarlo, Jr. et al. |
| 6,364,910 B1 | 4/2002 | Shultz et al. |
| 6,368,352 B1 | 4/2002 | Camino et al. |
| 6,379,386 B1 | 4/2002 | Resch et al. |
| 6,406,495 B1 | 6/2002 | Schoch |
| 6,423,096 B1 | 7/2002 | Musset et al. |
| 6,428,578 B2 | 8/2002 | White |
| 6,447,549 B1 | 9/2002 | Taft |
| 6,458,161 B1 | 10/2002 | Gibbs et al. |
| 6,613,092 B1 | 9/2003 | Kana et al. |
| 6,682,568 B2 | 1/2004 | Despres, III et al. |
| 6,699,293 B2 | 3/2004 | White |
| 6,783,549 B1 | 8/2004 | Stone et al. |
| 6,797,006 B2 | 9/2004 | Hodorek |
| 6,818,019 B2 | 11/2004 | Horber |
| 6,843,806 B2 | 1/2005 | Hayes et al. |
| 6,875,218 B2 | 4/2005 | Dye et al. |
| 6,875,237 B2 | 4/2005 | Dye et al. |
| 6,911,047 B2 | 6/2005 | Rockwood, Jr. et al. |
| 6,926,740 B2 | 8/2005 | Lewis et al. |
| 6,946,001 B2 | 9/2005 | Sanford et al. |
| 6,981,991 B2 | 1/2006 | Ferree |
| 7,105,026 B2 | 9/2006 | Johnson et al. |
| 7,179,295 B2 | 2/2007 | Kovacevic |
| 7,179,296 B2 | 2/2007 | Dooney |
| 7,179,297 B2 | 2/2007 | McLean |

(56) References Cited

U.S. PATENT DOCUMENTS

| | | |
|---|---|---|
| 7,179,298 B2 | 2/2007 | Greenlee |
| D538,431 S | 3/2007 | Botha |
| 7,238,208 B2 | 7/2007 | Camino et al. |
| 7,264,636 B2 | 9/2007 | Lewis et al. |
| 7,291,174 B2 | 11/2007 | German et al. |
| 7,291,177 B2 | 11/2007 | Gibbs |
| 7,435,263 B2 | 10/2008 | Barnett et al. |
| 7,713,306 B2 | 5/2010 | Gibbs |
| D618,800 S | 6/2010 | Mayon et al. |
| 7,753,959 B2 | 7/2010 | Berelsman et al. |
| 7,846,212 B2 | 12/2010 | Lewis et al. |
| 7,892,288 B2 | 2/2011 | Blaylock et al. |
| 7,892,289 B2 | 2/2011 | Serafin, Jr. et al. |
| 8,123,814 B2 | 2/2012 | Meridew et al. |
| 8,382,849 B2 | 2/2013 | Thomas |
| D684,693 S | 6/2013 | Hanssen et al. |
| 8,506,645 B2 | 8/2013 | Blaylock et al. |
| 8,535,385 B2 | 9/2013 | Hanssen et al. |
| 8,696,677 B2 | 4/2014 | Chavarria |
| 8,728,168 B2 | 5/2014 | Hanssen et al. |
| 8,876,907 B2 | 11/2014 | Baptista et al. |
| 9,044,326 B2 | 6/2015 | Blaylock et al. |
| 9,192,476 B2 | 11/2015 | Thomas et al. |
| 9,265,614 B2 | 2/2016 | Blaylock et al. |
| 9,539,096 B2 | 1/2017 | Hanssen et al. |
| 9,713,532 B2 | 7/2017 | Blaylock et al. |
| 9,713,533 B2 | 7/2017 | Taylor et al. |
| 9,907,664 B2 | 3/2018 | Blaylock et al. |
| 10,085,841 B2 | 10/2018 | Blaylock et al. |
| 10,092,404 B2 | 10/2018 | Hanssen et al. |
| 10,098,743 B2 | 10/2018 | Hanssen et al. |
| 10,195,043 B2 | 2/2019 | Taylor et al. |
| 10,201,426 B2 | 2/2019 | Hanssen et al. |
| 10,646,346 B2 | 5/2020 | Hanssen et al. |
| 10,653,526 B2 | 5/2020 | Hanssen et al. |
| 10,806,587 B2 | 10/2020 | Hanssen et al. |
| 11,141,276 B2 | 10/2021 | Kehres |
| 2001/0037153 A1 | 11/2001 | Charles, Jr. et al. |
| 2002/0072802 A1 | 6/2002 | O'Neil et al. |
| 2002/0095214 A1 | 7/2002 | Hyde, Jr. |
| 2002/0120339 A1 | 8/2002 | Callaway et al. |
| 2002/0151984 A1 | 10/2002 | White |
| 2003/0055507 A1 | 3/2003 | Mcdevitt et al. |
| 2003/0065397 A1 | 4/2003 | Hanssen et al. |
| 2003/0153981 A1 | 8/2003 | Wang et al. |
| 2003/0163203 A1 | 8/2003 | Nycz et al. |
| 2003/0183025 A1 | 10/2003 | Krstic |
| 2003/0204263 A1 | 10/2003 | Justin et al. |
| 2003/0229398 A1 | 12/2003 | Iesaka |
| 2004/0034432 A1 | 2/2004 | Hughes et al. |
| 2004/0049270 A1 | 3/2004 | Gewirtz |
| 2004/0049284 A1 | 3/2004 | German et al. |
| 2004/0059424 A1 | 3/2004 | Guederian et al. |
| 2004/0117024 A1 | 6/2004 | Gerbec et al. |
| 2004/0122519 A1 | 6/2004 | Wiley et al. |
| 2004/0162619 A1 | 8/2004 | Blaylock et al. |
| 2004/0172137 A1 | 9/2004 | Blaylock et al. |
| 2004/0220673 A1* | 11/2004 | Pria ................ A61F 2/4081 623/19.12 |
| 2004/0220674 A1 | 11/2004 | Pria |
| 2005/0060039 A1 | 3/2005 | Cyprien |
| 2005/0107882 A1 | 5/2005 | Stone et al. |
| 2005/0107883 A1 | 5/2005 | Goodfried et al. |
| 2005/0165494 A1 | 7/2005 | Mcleod et al. |
| 2005/0261775 A1 | 11/2005 | Baum et al. |
| 2005/0278034 A1 | 12/2005 | Johnson et al. |
| 2005/0283254 A1 | 12/2005 | Hayes, Jr. et al. |
| 2005/0288795 A1 | 12/2005 | Bagga et al. |
| 2006/0069443 A1 | 3/2006 | Deffenbaugh et al. |
| 2006/0069444 A1 | 3/2006 | Deffenbaugh |
| 2006/0079963 A1 | 4/2006 | Hansen |
| 2006/0122705 A1 | 6/2006 | Morgan |
| 2006/0149388 A1 | 7/2006 | Smith et al. |
| 2006/0200248 A1 | 9/2006 | Beguin et al. |
| 2007/0055380 A1 | 3/2007 | Berelsman et al. |
| 2007/0088443 A1 | 4/2007 | Hanssen et al. |
| 2007/0100458 A1* | 5/2007 | Dalia ................ A61F 2/4081 623/19.13 |
| 2007/0129809 A1 | 6/2007 | Meridew et al. |
| 2007/0142917 A1 | 6/2007 | Roche et al. |
| 2007/0156246 A1 | 7/2007 | Meswania et al. |
| 2007/0173948 A1 | 7/2007 | Meridew et al. |
| 2007/0219637 A1 | 9/2007 | Berelsman et al. |
| 2007/0219638 A1 | 9/2007 | Jones |
| 2007/0225817 A1 | 9/2007 | Reubelt et al. |
| 2007/0225818 A1 | 9/2007 | Reubelt et al. |
| 2007/0244563 A1 | 10/2007 | Roche et al. |
| 2007/0244564 A1 | 10/2007 | Ferrand et al. |
| 2008/0167722 A1 | 7/2008 | Metzger et al. |
| 2008/0269906 A1 | 10/2008 | Iannotti et al. |
| 2008/0281430 A1 | 11/2008 | Kelman et al. |
| 2009/0125113 A1 | 5/2009 | Guederian et al. |
| 2009/0149961 A1 | 6/2009 | Dallmann |
| 2009/0164021 A1 | 6/2009 | Dallmann |
| 2009/0192621 A1 | 7/2009 | Winslow et al. |
| 2010/0049327 A1 | 2/2010 | Isch et al. |
| 2010/0114326 A1 | 5/2010 | Winslow et al. |
| 2010/0145452 A1 | 6/2010 | Blaylock et al. |
| 2010/0241235 A1 | 9/2010 | Basamania et al. |
| 2919/0228352 | 9/2010 | Courtney, Jr. et al. |
| 2010/0324691 A1 | 12/2010 | Brunnarius |
| 2011/0035013 A1 | 2/2011 | Winslow et al. |
| 2011/0066252 A1 | 3/2011 | Hanssen et al. |
| 2011/0112651 A1 | 5/2011 | Blaylock et al. |
| 2011/0118846 A1 | 5/2011 | Katrana et al. |
| 2011/0276144 A1 | 11/2011 | Wirth et al. |
| 2011/0282403 A1 | 11/2011 | Anthony et al. |
| 2011/0295382 A1 | 12/2011 | Hanssen |
| 2012/0109321 A1 | 5/2012 | Stone et al. |
| 2012/0130498 A1 | 5/2012 | Long |
| 2012/0130499 A1 | 5/2012 | Long et al. |
| 2012/0179262 A1 | 7/2012 | Metcalfe et al. |
| 2012/0221111 A1 | 8/2012 | Burkhead, Jr. et al. |
| 2012/0239051 A1 | 9/2012 | De Wilde et al. |
| 2012/0239155 A1 | 9/2012 | De Wilde et al. |
| 2012/0277880 A1 | 11/2012 | Winslow et al. |
| 2013/0013078 A1 | 1/2013 | Hanssen et al. |
| 2013/0013080 A1 | 1/2013 | Hanssen et al. |
| 2013/0018478 A1 | 1/2013 | Hanssen et al. |
| 2013/0123929 A1 | 5/2013 | Mcdaniel et al. |
| 2013/0144393 A1 | 6/2013 | Mutchler et al. |
| 2013/0150975 A1* | 6/2013 | Iannotti ................ A61F 2/4059 623/19.11 |
| 2013/0190881 A1 | 7/2013 | Winslow et al. |
| 2013/0253658 A1 | 9/2013 | Despres et al. |
| 2013/0261753 A1 | 10/2013 | Lappin et al. |
| 2013/0261754 A1 | 10/2013 | Anthony et al. |
| 2013/0304221 A1 | 11/2013 | Blaylock et al. |
| 2014/0005789 A1 | 1/2014 | Chavarria et al. |
| 2014/0031945 A1 | 1/2014 | Baptista et al. |
| 2014/0039638 A1 | 2/2014 | Meridew et al. |
| 2014/0074250 A1 | 3/2014 | Podolsky et al. |
| 2014/0081418 A1 | 3/2014 | Hanssen et al. |
| 2014/0128983 A1 | 5/2014 | Flaherty et al. |
| 2014/0194995 A1* | 7/2014 | Koka ................ A61F 2/4637 623/19.11 |
| 2014/0249637 A1 | 9/2014 | Hanssen et al. |
| 2014/0257499 A1 | 9/2014 | Winslow et al. |
| 2014/0277518 A1 | 9/2014 | Iannotti |
| 2015/0150688 A1 | 6/2015 | Vanasse et al. |
| 2015/0250602 A1* | 9/2015 | Sikora ................ A61F 2/4081 623/19.12 |
| 2015/0257890 A1 | 9/2015 | Blaylock et al. |
| 2015/0272741 A1 | 10/2015 | Taylor et al. |
| 2015/0374502 A1 | 12/2015 | Hodorek et al. |
| 2016/0008138 A1 | 1/2016 | Katrana et al. |
| 2016/0058560 A1 | 3/2016 | Blaylock et al. |
| 2016/0151164 A1 | 6/2016 | Taylor et al. |
| 2016/0184103 A1 | 6/2016 | Fonte et al. |
| 2016/0262902 A1 | 9/2016 | Winslow et al. |
| 2016/0270922 A1 | 9/2016 | Pressacco et al. |
| 2016/0310285 A1 | 10/2016 | Kovacs et al. |
| 2017/0020675 A1 | 1/2017 | Blaylock et al. |
| 2017/0281357 A1 | 10/2017 | Taylor et al. |

(56) References Cited

U.S. PATENT DOCUMENTS

| | | | |
|---|---|---|---|
| 2018/0098856 A1 | 4/2018 | Blaylock et al. | |
| 2018/0256337 A1 | 9/2018 | Hanssen et al. | |
| 2019/0000632 A1 | 1/2019 | Blaylock et al. | |
| 2019/0336293 A1 | 11/2019 | Kehres | |

FOREIGN PATENT DOCUMENTS

| | | | | |
|---|---|---|---|---|
| CN | 102014802 A | 4/2011 | | |
| CN | 103519923 A | 1/2014 | | |
| CN | 103702627 A | 4/2014 | | |
| CN | 107205824 A | 9/2017 | | |
| CN | 110191691 A | 8/2019 | | |
| DE | 102010044571 A1 | 3/2012 | | |
| EP | 0336774 B1 | 12/1992 | | |
| EP | 0532585 B1 | 4/2000 | | |
| EP | 1004283 A2 | 5/2000 | | |
| EP | 0863731 B1 | 4/2001 | | |
| EP | 1004283 A3 | 3/2002 | | |
| EP | 1004283 B1 | 5/2005 | | |
| EP | 1913902 A1 | 4/2008 | | |
| EP | 2130518 A1 | 12/2009 | | |
| EP | 2679199 A1 | 1/2014 | | |
| EP | 2689751 A1 | 1/2014 | | |
| EP | 2822508 | 1/2015 | | |
| FR | 2702651 A1 | 9/1994 | | |
| FR | 2772593 A1 | 6/1999 | | |
| FR | 2932377 A1 * | 12/2009 | ............... | A61F 2/40 |
| FR | 2937245 B1 | 5/2012 | | |
| FR | 2971416 A1 | 8/2012 | | |
| GB | 2223172 A | 4/1990 | | |
| JP | 6169930 A | 6/1994 | | |
| JP | 10277069 A | 10/1998 | | |
| JP | 2000185062 A | 7/2000 | | |
| JP | 2001503283 A | 3/2001 | | |
| JP | 2001526573 A | 12/2001 | | |
| JP | 2004016822 A | 1/2004 | | |
| JP | 2005246036 A | 9/2005 | | |
| JP | 2009513285 A | 4/2009 | | |
| JP | 2016513498 A | 5/2016 | | |
| JP | 2017536195 A | 12/2017 | | |
| WO | WO-9730661 A1 | 8/1997 | | |
| WO | WO-9852499 A1 | 11/1998 | | |
| WO | WO-9932053 A1 | 7/1999 | | |
| WO | WO-0205732 A1 | 1/2002 | | |
| WO | WO-2007109319 A2 | 9/2007 | | |
| WO | WO-2009089581 A1 | 7/2009 | | |
| WO | WO-2013134333 A1 | 9/2013 | | |
| WO | WO-20150130006 A1 | 9/2015 | | |
| WO | WO-2015148655 A1 | 10/2015 | | |
| WO | WO-2016089642 A1 | 6/2016 | | |
| WO | WO-2018136393 A1 | 7/2018 | | |

OTHER PUBLICATIONS

U.S. Appl. No. 14/085,040 U.S. Pat. No. 9,539,096, filed Nov. 20, 2013, Methods for Supporting a Prosthetic Implant Implant in a Patient.
U.S. Appl. No. 14/278,916 U.S. Pat. No. 10,653,526, filed May 15, 2014, Prosthetic Implant Support Structure.
U.S. Appl. No. 15/978,686 U.S. Pat. No. 10,806,587, filed May 14, 2018, Prosthetic Implant Support Structure.
U.S. Appl. No. 10/225,774, filed Aug. 22, 2002, Prosthetic Implant Support Structure.
U.S. Appl. No. 11/560,276 U.S. Pat. No. 10,201,426, filed Nov. 15, 2006, Prosthetic Implant Support Structure.
U.S. Appl. No. 12/946,132 U.S. Pat. No. 8,728,168, filed Nov. 15, 2020, Prosthetic Implant Support Sturcture.
U.S. Appl. No. 29/379,094 D684,693, filed Nov. 15, 2010, Prosthetic Implant Support Structure.
U.S. Appl. No. 13/205,163 U.S. Pat. No. 8,535,385, filed Aug. 8, 2011, Prosthetic Implant Support Structure.
U.S. Appl. No. 12/702,861, filed Feb. 9, 2010, Prosthetic Implant Support Structure.
U.S. Appl. No. 13/619,091 U.S. Pat. No. 10,098,743, filed Sep. 14, 2012, Prosthetic Implant Support Structure.
U.S. Appl. No. 13/619,134 U.S. Pat. No. 10,092,404, filed Sep. 14, 2012, Prosthetic Implant Support Structure.
U.S. Appl. No. 13/619,190 U.S. Pat. No. 10,646,346, filed Sep. 14, 2012, Prosthetic Implant Support Structure.
U.S. Appl. No. 16/475,215, filed Jul. 1, 2019, Modular Augment Component.
U.S. Appl. No. 14/226,051, filed Mar. 26, 2014, Press-Fit Glenoid With Peripheral Compression Pegs.
U.S. Appl. No. 14/558,024 U.S. Pat. No. 9,713,533, filed Dec. 2, 2014, In-Line Pegged Hybrid Glenoid.
U.S. Appl. No. 15/629,794 U.S. Pat. No. 10,195,043, filed Jun. 22, 2017, In-Line Pegged Hybrid Glenoid.
US 5,536,414, Oct. 1994, Cohen et al. (withdrawn)
"U.S. Appl. No. 10/225,774, Advisory Action dated Oct. 26, 2005", 3 pgs.
"U.S. Appl. No. 10/225,774, Examiner Interview Summary dated Mar. 17, 2005", 4 pgs.
"U.S. Appl. No. 10/225,774, Final Office Action dated Jun. 6, 2005", 9 pgs.
"U.S. Appl. No. 10/225,774, Final Office Action dated Aug. 17, 2006", 8 pgs.
"U.S. Appl. No. 10/225,774, Non-Final Office Action dated Feb. 8, 2006", 6 pgs.
"U.S. Appl. No. 10/225,774, Non-Final Office Action dated Jun. 30, 2004", 5 pgs.
"U.S. Appl. No. 10/225,774, Non-Final Office Action dated Dec. 8, 2004", 6 pgs.
"U.S. Appl. No. 10/225,774, Response filed Mar. 7, 2005 to Non-Final Office Action dated Dec. 8, 2004", 21 pgs.
"U.S. Appl. No. 10/225,774, Response filed Apr. 16, 2004 to Restriction Requirement dated Mar. 17, 2004", 1 pg.
"U.S. Appl. No. 10/225,774, Response filed Jun. 7, 2006 to Non-Final Office Action datled Feb. 8, 2006", 21 pgs.
"U.S. Appl. No. 10/225,774, Response filed Sep. 20, 2004 to Non-Final Office Action dated Jun. 30, 2004", 14 pgs.
"U.S. Appl. No. 10/225,774, Response filed Oct. 6, 2005 to Final Office Action dated Jun. 6, 2005", 21 pgs.
"U.S. Appl. No. 10/780,378, Response filed Nov. 15, 2006 to Final Office Action dated Aug. 17, 2006", 1 pg.
"U.S. Appl. No. 10/780,378, Restriction Requirement dated Mar. 17, 2004", 6 pgs.
"U.S. Appl. No. 10/780,378, Final Office Action dated Apr. 20, 2010", 7 pgs.
"U.S. Appl. No. 10/780,378, Final Office Action dated Aug. 21, 2008", 8 pgs.
"U.S. Appl. No. 10/780,378, Final Office Action dated Aug. 27, 2007", 7 pgs.
"U.S. Appl. No. 10/780,378, Non Final Office Action dated Feb. 2, 2009", 7 pgs.
"U.S. Appl. No. 10/780,378, Non Final Office Action dated Mar. 30, 2007", 7 pgs.
"U.S. Appl. No. 10/780,378, Non Final Office Action dated Dec. 12, 2007", 8 pgs.
"U.S. Appl. No. 10/780,378, Preliminary Amendment filed Jun. 1, 2004", 20 pgs.
"U.S. Appl. No. 10/780,378, Response filed Jan. 4, 2007 to Restriction Requirement dated Dec. 4, 2006", 1 pg.
"U.S. Appl. No. 10/780,378, Response filed May 28, 2008 to Non-Final Office Action mailed Dec. 12, 2007", 11 pgs.
"U.S. Appl. No. 10/780,378, Response filed Jun. 15, 2007 to Non-Final Office Action dated Mar. 30, 2007", 7 pgs.
"U.S. Appl. No. 10/780,378, Response filed Jun. 24, 2009 to Non-Final Office Action dated Feb. 2, 2009", 15 pgs.
"U.S. Appl. No. 10/780,378, Response filed Sep. 15, 2006 to Restriction Requirement dated Aug. 25, 2006", 1 pg.
"U.S. Appl. No. 10/780,378, Response filed Oct. 31, 2007 to Final Office Action dated Aug. 27, 2007", 8 pgs.
"U.S. Appl. No. 10/780,378, Response filed Nov. 12, 2008 to Final Office Action dated Aug. 21, 2008", 10 pgs.
"U.S. Appl. No. 10/780,378, Response filed Dec. 22, 2009 to Restriction Requirement dated Oct. 22, 2009", 2 pgs.

(56) References Cited

OTHER PUBLICATIONS

"U.S. Appl. No. 10/780,378, Restriction Requirement dated Aug. 25, 2006", 6 pgs.
"U.S. Appl. No. 10/780,378, Restriction Requirement dated Oct. 22, 2009", 7 pgs.
"U.S. Appl. No. 10/780,378, Restriction Requirement dated Dec. 4, 2006", 6 pgs.
"U.S. Appl. No. 10/794,721, Final Office Action dated Jan. 16, 2008", 8 pgs.
"U.S. Appl. No. 10/794,721, Final Office Action dated Jan. 16, 2009", 6 pgs.
"U.S. Appl. No. 10/794,721, Final Office Action dated May 6, 2010", 8 pgs.
"U.S. Appl. No. 10/794,721, Non Final Office Action dated Jul. 8, 2008", 6 pgs.
"U.S. Appl. No. 10/794,721, Non Final Office Action dated Aug. 3, 2007", 7 pgs.
"U.S. Appl. No. 10/794,721, Non Final Office Action dated Nov. 2, 2006", 7 pgs.
"U.S. Appl. No. 10/794,721, Non-Final Office Action dated Jun. 15, 2009", 9 pgs.
"U.S. Appl. No. 10/794,721, Notice of Allowance dated Oct. 14, 2010", 6 pgs.
"U.S. Appl. No. 10//94,721, Response filed Feb. 2, 2007 to Non Final Office Action dated Nov. 2, 2006", 7 pgs.
"U.S. Appl. No. 10/794,721, Response filed Apr. 14, 2009 to Final Office Action dated Jan. 16, 2009", 8 pgs.
"U.S. Appl. No. 10/794,721, Response filed Jun. 16, 2008 to Final Office Action dated Jan. 16, 2008", 8 pgs.
"U.S. Appl. No. 10/794,721, Response filed Sep. 28, 2009 to Non Final Office Action dated Jun. 15, 2009", 10 pgs.
"U.S. Appl. No. 10/794,721, Response filed Oct. 6, 2010 to Final Office Action dated May 6, 2010", 6 pgs.
"U.S. Appl. No. 10/794,721, Response filed Oct. 8, 2008 to Non Final Office Action dated Jul. 8, 2008", 8 pgs.
"U.S. Appl. No. 10/794,721, Response filed Nov. 8, 2007 to Non Final Office Action dated Aug. 3, 2007", 7 pgs.
"U.S. Appl. No. 10/794,721, Supplemental Response filed Feb. 8, 2010 to Non Final Office Action dated Jan. 12, 2010", 2 pgs.
"U.S. Appl. No. 10/794,721, Supplemental Response filed May 18, 2007 to Non Final Office Action dated Nov. 2, 2006", 7 pgs.
"U.S. Appl. No. 11/560,276, Appeal Brief filed Oct. 27, 2016", 68 pgs.
"U.S. Appl. No. 11/560,276, Appeal Decision dated Apr. 16, 2018", 16 pgs.
"U.S. Appl. No. 11/560,276, Appellants' Reply Brief filed Feb. 1, 2017 to Examiner's Answer dated Dec. 1, 2016", 15 pgs.
"U.S. Appl. No. 11/560,276, Examiner Interview Summary dated Jan. 18, 2012", 4 pgs.
"U.S. Appl. No. 11/560,276, Examiner Interview Summary dated Jun. 5, 2012", 3 pgs.
"U.S. Appl. No. 11/560,276, Final Office Action dated Feb. 26, 2016", 17 pgs.
"U.S. Appl. No. 11/560,276, Final Office Action dated Mar. 27, 2012", 8 pgs.
"U.S. Appl. No. 11/560,276, Final Office Action dated May 1, 2015", 16 pgs.
"U.S. Appl. No. 11/560,276, Final Office Action dated Jun. 25, 2014", 10 pgs.
"U.S. Appl. No. 11/560,276, Final Office Action dated Oct. 8, 2010", 6 pgs.
"U.S. Appl. No. 11/560,276, Final Office Action dated Oct. 17, 2013", 12 pgs.
"U.S. Appl. No. 11/560,276, Non Final Office Action dated Jan. 22, 2014", 10 pgs.
"U.S. Appl. No. 11/560,276, Non Final Office Action dated Mar. 3, 2010", 8 pgs.
"U.S. Appl. No. 11/560,276, Non Final Office Action dated Aug. 11, 2011", 6 pgs.
"U.S. Appl. No. 11/560,276, Non Final Office Action dated Sep. 25, 2015", 16 pgs.
"U.S. Appl. No. 11/560,276, Non Final Office Action dated Dec. 5, 2014", 14 pgs.
"U.S. Appl. No. 11/560,276, Notice of Allowance dated Jul. 13, 2018", 6 pgs.
"U.S. Appl. No. 11/560,276, Notice of Allowance dated Oct. 2, 2018", 6 pgs.
"U.S. Appl. No. 11/560,276, Response filed Jan. 25, 2016 to Non-Final Office Action dated Sep. 25, 2015", 33 pgs.
"U.S. Appl. No. 11/560,276, Response filed Feb. 7, 2011 to Final Office Action dated Oct. 8, 2010", 10 pgs.
"U.S. Appl. No. 11/560,276, Response filed Feb. 13, 2012 to Non Final Office Action dated Aug. 11, 2011", 13 pgs.
"U.S. Appl. No. 11/560,276, Response filed Apr. 6, 2015 to Non-Final Office Action dated Dec. 5, 2014", 16 pgs.
"U.S. Appl. No. 11/560,276, Response filed May 22, 2014 to Non Final Office Action dated Jan. 22, 2014", 10 pgs.
"U.S. Appl. No. 11/560,276, Response filed Jun. 27, 2012 to Final Office Action dated Mar. 27, 2012", 12 pgs.
"U.S. Appl. No. 11/560,276, Response filed Aug. 2, 2010 to Non Final Office Action dated Mar. 3, 2010", 12 pgs.
"U.S. Appl. No. 11/560,276, Response filed Sep. 1, 2015 to Final Office Action dated May 1, 2015", 28 pgs.
"U.S. Appl. No. 11/560,276, Response filed Oct. 21, 2009 to Restriction Requirement dated Aug. 21, 2009", 12 pgs.
"U.S. Appl. No. 11/560,276, Response filed Oct. 27, 2014 to Final Office Action dated Jun. 25, 2014", 13 pgs.
"U.S. Appl. No. 11/560,276, Response filed Dec. 17, 2013 to Final Office Action dated Oct. 17, 2013", 11 pgs.
"U.S. Appl. No. 11/560,276, Restriction Requirement dated Aug. 21, 2009", 7 pgs.
"U.S. Appl. No. 12/886,297, Examiner Interview Summary dated May 6, 2013", 3 pgs.
"U.S. Appl. No. 12/886,297, Final Office Action dated Nov. 16, 2012", 6 pgs.
"U.S. Appl. No. 12/886,297, Non Final Office Action dated Apr. 22, 2013", 6 pgs.
"U.S. Appl. No. 12/886,297, Non Final Office Action dated Jun. 21, 2012", 10 pgs.
"U.S. Appl. No. 12/886,297, Notice of Allowance dated Feb. 22, 2013", 10 pgs.
"U.S. Appl. No. 12/886,297, Notice of Allowance dated Jun. 26, 2013", 10 pgs.
"U.S. Appl. No. 12/886,297, Preliminary Amendment filed Sep. 20, 2010", 10 pgs.
"U.S. Appl. No. 12/886,297, Response filed May 7, 2012 to Restriction Requirement dated Mar. 6, 2012", 2 pgs.
"U.S. Appl. No. 12/886,297, Response filed Oct. 22, 2012 to Non Final Office Action dated Jun. 21, 2012", 19 pgs.
"U.S. Appl. No. 12/886,297, Restriction Requirement dated Mar. 6, 2012", 6 pgs.
"U.S. Appl. No. 12/946,132, Examiner Interview Summary dated Jun. 5, 2012", 3 pgs.
"U.S. Appl. No. 12/946,132, Final Office Action dated Jul. 25, 2012", 12 pgs.
"U.S. Appl. No. 12/946,132, Non Final Office Action dated Mar. 28, 2012", 10 pgs.
"U.S. Appl. No. 12/946,132, Non Final Office Action dated Oct. 11, 2013", 7 pgs.
"U.S. Appl. No. 12/946,132, Notice of Allowance dated Mar. 27, 2014", 6 pgs.
"U.S. Appl. No. 12/946,132, Response filed Feb. 11, 2014 to Non-Final Office Action dated Oct. 11, 2013", 19 pgs.
"U.S. Appl. No. 12/946,132, Response filed Jun. 27, 2012 to Non Final Office Action dated Mar. 28, 2012", 15 pgs.
"U.S. Appl. No. 12/946,132, Response filed Sep. 6, 2011 to Restriction Requirement dated Aug. 23, 2011", 8 pgs.
"U.S. Appl. No. 12/946,132, Response filed Sep. 24, 2012 to Final Office Action dated Jul. 25, 2012", 16 pgs.
"U.S. Appl. No. 12/946,132, Restriction Requirement dated Aug. 23, 2011", 8 pgs.

(56) References Cited

OTHER PUBLICATIONS

"U.S. Appl. No. 13/007,225, Examiner Interview Summary dated May 30, 2013", 23 pgs.

"U.S. Appl. No. 13/007,225, Final Office Action dated Apr. 18, 2013", 10 pgs.

"U.S. Appl. No. 13/007,225, Final Office Action dated Jun. 25, 2014", 11 pgs.

"U.S. Appl. No. 13/007,225, Non Final Office Action dated Jan. 29, 2014", 11 pgs.

"U.S. Appl. No. 13/007,225, Non Final Office Action dated Nov. 19, 2012", 9 pgs.

"U.S. Appl. No. 13/007,225, Non Final Office Action dated Dec. 11, 2014", 6 pgs.

"U.S. Appl. No. 13/007,225, Notice of Allowance dated Apr. 6, 2015", 10 pgs.

"U.S. Appl. No. 13/007,225, Preliminary Amendment filed Jan. 14, 2011", 4 pgs.

"U.S. Appl. No. 13/007,225, Response filed Mar. 3, 2015 to Non-Final Office Action dated Dec. 11, 2014", 13 pgs.

"U.S. Appl. No. 13/007,225, Response filed Mar. 12, 2013 to Non-Final Office Action dated Nov. 19, 2012", 13 pgs.

"U.S. Appl. No. 13/007,225, Response filed May 29, 2014 to Non Final Office Action dated Jan. 29, 2014", 12 pgs.

"U.S. Appl. No. 13/007,225, Response filed Jul. 18, 2013 to Final Office Action dated Apr. 18, 2013", 15 pgs.

"U.S. Appl. No. 13/007,225, Response filed Oct. 22, 2012 to Restriction Requirement dated Sep. 20, 2012", 10 pgs.

"U.S. Appl. No. 13/007,225, Response filed Oct. 27, 2014 to Final Office Action dated Jun. 25, 2014", 16 pgs.

"U.S. Appl. No. 13/007,225, Restriction Requirement dated Sep. 20, 2012", 8 pgs.

"U.S. Appl. No. 13/007,225, Supplemental Preliminary Amendment filed Sep. 23, 2011", 8 pgs.

"U.S. Appl. No. 13/205,163, Non Final Office Action dated Apr. 4, 2013", 8 pgs.

"U.S. Appl. No. 13/205,163, Notice of Allowance dated Aug. 5, 2013", 9 pgs.

"U.S. Appl. No. 13/205,163, Preliminary Amendment filed Aug. 8, 2011", 8 pgs.

"U.S. Appl. No. 13/205,163, Response filed Feb. 21, 2013 to Restriction Requirement dated Jan. 24, 2013", 10 pgs.

"U.S. Appl. No. 13/205,163, Response filed Jul. 3, 2013 to Non Final Office Action dated Apr. 4, 2013", 13 pgs.

"U.S. Appl. No. 13/205,163, Restriction Requirement dated Jan. 24, 2013", 6 pgs.

"U.S. Appl. No. 13/416,857, Non Final Office Action dated Feb. 25, 2013", 17 pgs.

"U.S. Appl. No. 13/619,091, Response filed May 24, 2013 to Non Final Office Action dated Feb. 25, 2013", 15 pgs.

"U.S. Appl. No. 13/619,091, Advisory Action dated Sep. 17, 2014", 3 pgs.

"U.S. Appl. No. 13/619,091, Appeal Brief filed Feb. 11, 2016", 103 pgs.

"U.S. Appl. No. 13/619,091, Appeal Brief filed Dec. 19, 2016", 113 pgs.

"U.S. Appl. No. 13/619,091, Appeal Decision dated Apr. 27, 2018", 32 pgs.

"U.S. Appl. No. 13/619,091, Examiner Interview Summary dated Sep. 8, 2014", 3 pgs.

"U.S. Appl. No. 13/619,091, Final Office Action dated Mar. 10, 2015", 18 pgs.

"U.S. Appl. No. 13/619,091, Final Office Action dated May 9, 2014", 10 pgs.

"U.S. Appl. No. 13/619,091, Final Office Action dated Oct. 11, 2016", 21 pgs.

"U.S. Appl. No. 13/619,091, Final Office Action dated Dec. 2, 2015", 19 pgs.

"U.S. Appl. No. 13/619,091, Non Final Office Action dated Jun. 22, 2016", 22 pgs.

"U.S. Appl. No. 13/619,091, Non Final Office Action dated Jul. 1, 2015", 17 pgs.

"U.S. Appl. No. 13/619,091, Non Final Office Action dated Dec. 4, 2014", 15 pgs.

"U.S. Appl. No. 13/619,091, Non Final Office Action dated Dec. 13, 2013", 11 pgs.

"U.S. Appl. No. 13/619,091, Notice of Allowance dated Sep. 4, 2018", 7 pgs.

"U.S. Appl. No. 13/619,091, Notice of Non-Compiiant Amendment dated Jul. 17, 2018", 2 pgs.

"U.S. Appl. No. 13/619,091, Preliminary Amendment filed Aug. 26, 2013", 7 pgs.

"U.S. Appl. No. 13/619,091, Reply Brief filed Apr. 3, 2017", 11 pgs.

"U.S. Appl. No. 13/619,091, Response filed Jan. 21, 2015 to Non-Final Office Action dated Dec. 4, 2014", 31 pgs.

"U.S. Appl. No. 13/619,091, Response filed Apr. 14, 2014 to Non-Final Office Action dated Dec. 13, 2013", 13 pgs.

"U.S. Appl. No. 13/619,091, Response filed Jun. 10, 2015 to Final Office Action dated Mar. 10, 2015", 32 pgs.

"U.S. Appl. No. 13/619,091, Response filed Aug. 1, 2018 to Notice of Non-Compliant Amendment dated Jul. 17, 2018", 17 pgs.

"U.S. Appl. No. 13/619,091, Response filed Sep. 9, 2014 to Final Office Action dated May 9, 2014", 12 pgs.

"U.S. Appl. No. 13/619,091, Response filed Sep. 22, 2016 to Non Final Office Action dated Jun. 22, 2016", 34 pgs.

"U.S. Appl. No. 13/619,091, Response filed Oct. 9, 2014 to Advisory Action dated Sep. 17, 2014", 14 pgs.

"U.S. Appl. No. 13/619,091, Response filed Nov. 8, 2013 to Restriction Requirement dated Oct. 23, 2013", 8 pgs.

"U.S. Appl. No. 13/619,134, Response filed Nov. 10, 2015 to Non-Final Office Action dated Jul. 1, 2015", 37 pgs.

"U.S. Appl. No. 13/619,134, Restriction Requirement dated Oct. 23, 13", 5 pgs.

"U.S. Appl. No. 13/619,134, Advisory Action dated Sep. 18, 2014", 3 pgs.

"U.S. Appl. No. 13/619,134, Appeal Brief filed Feb. 4, 2016", 72 pgs.

"U.S. Appl. No. 13/619,134, Appeal Brief filed Dec. 19, 2016", 112 pgs.

"U.S. Appl. No. 13/619,134, Appeal Decision mailed May 1, 2018", 32 pgs.

"U.S. Appl. No. 13/619,134, Appellant's Reply Brief filed May 19, 2017", 14 pgs.

"U.S. Appl. No. 13/619,134, Examiner's Answer dated Mar. 20, 2017", 15 pgs.

"U.S. Appl. No. 13/619,134, Final Office Action dated Mar. 10, 2015", 20 pgs.

"U.S. Appl. No. 13/619,134, Final Office Action dated May 8, 2014", 10 pgs.

"U.S. Appl. No. 13/619,134, Final Office Action dated Oct. 11, 2016", 25 pgs.

"U.S. Appl. No. 13/619,134, Final Office Action dated Dec. 2, 2015", 21 pgs.

"U.S. Appl. No. 13/619,134, Non Final Office Action dated Jun. 22, 2016", 24 pgs.

"U.S. Appl. No. 13/619,134, Non Final Office Action dated Jul. 6, 2015", 19 pgs.

"U.S. Appl. No. 13/619,134, Non Final Office Action dated Dec. 5, 2014", 18 pgs.

"U.S. Appl. No. 13/619,134, Non Final Office Action dated Dec. 13, 2013", 9 pgs.

"U.S. Appl. No. 13/619,134, Notice of Allowance dated Aug. 29, 2018", 7 pgs.

"U.S. Appl. No. 13/619,134, Notice of Non-Compliant Amendment dated Jul. 17, 2018", 2 pgs.

"U.S. Appl. No. 13/619,134, Response filed Jan. 22, 2015 to Non-Final Office Action dated Dec. 5, 2014", 32 pgs.

"U.S. Appl. No. 13/619,134, Response filed Apr. 14, 2014 to Non-Final Office Action dated Dec. 13, 2013", 11 pgs.

"U.S. Appl. No. 13/619,134, Response filed Jun. 10, 2015 to Non-Final Office Action dated Mar. 10, 2015", 33 pgs.

"U.S. Appl. No. 13/619,134, Response filed Aug. 1, 2018 to Notice of Non-Compliant Amendment dated Jul. 17, 18", 17 pgs.

(56) References Cited

OTHER PUBLICATIONS

"U.S. Appl. No. 13/619,134, Response filed Sep. 8, 2014 to Final Office Action dated May 8, 2014", 13 pgs.
"U.S. Appl. No. 13/619,134, Response filed Sep. 22, 2016 to Non-Final Office Action mailed Jun. 22, 2016", 35 pgs.
"U.S. Appl. No. 13/619,134, Response filed Oct. 9, 2014 to Advisory Action dated Sep. 18, 2014", 14 pgs.
"U.S. Appl. No. 13/619,134, Response filed Nov. 8, 2013 to Restriction Requirement dated Oct. 17, 2013", 8 pgs.
"U.S. Appl. No. 13/619,134, Response filed Nov. 10, 2015 to Non Final Office Action dated Jul. 6, 2015", 39 pgs.
"U.S. Appl. No. 13/619,134, Restriction Requirement dated Oct. 17, 2013", 5 pgs.
"U.S. Appl. No. 13/619,190, Appeal Brief filed Aug. 9, 2017", 85 pgs.
"U.S. Appl. No. 13/619,190, Appeal Decision dated Jan. 2, 2020", 14 pgs.
"U.S. Appl. No. 13/619,190, Examiner's Answer dated Oct. 3, 2017", 9 pgs.
"U.S. Appl. No. 13/619,190, Final Office Action dated Mar. 1, 2016", 18 pgs.
"U.S. Appl. No. 13/619,190, Final Office Action dated Apr. 27, 2017", 17 pgs.
"U.S. Appl. No. 13/619,190, Final Office Action dated May 12, 2015", 16 pgs.
"U.S. Appl. No. 13/619,190, Final Office Action dated Jun. 25, 2014", 10 pgs.
"U.S. Appl. No. 13/619,190, Non Final Office Action dated Sep. 25, 2015", 17 pgs.
"U.S. Appl. No. 13/619,190, Non Final Office Action dated Oct. 27, 2016", 14 pgs.
"U.S. Appl. No. 13/619,190, Non Final Office Action dated Dec. 4, 2014", 14 pgs.
"U.S. Appl. No. 13/619,190, Non Final Office Action dated Dec. 18, 2013", 11 pgs.
"U.S. Appl. No. 13/619,190, Notice of Allowance dated Mar. 3, 2020", 7 pgs.
"U.S. Appl. No. 13/619,190, Preliminary Amendment filed Oct. 29, 2012", 8 pgs.
"U.S. Appl. No. 13/619,190, Reply Brief filed Nov. 28, 2017", 16 pgs.
"U.S. Appl. No. 13/619,190, Response filed Jan. 25, 2016 to Non-Final Office Action dated Sep. 25, 205", 35 pgs.
"U.S. Appl. No. 13/619,190, Response filed Mar. 22, 2017 to Non Final Office Action dated Oct. 27, 2016", 39 pgs.
"U.S. Appl. No. 13/619,190, Response filed Apr. 6, 2015 to Non-Final Office Action dated Dec. 4, 2014", 17 pgs.
"U.S. Appl. No. 13/619,190, Response filed May 19, 2014 to Non Final Office Action dated Dec. 18, 2013", 12 pgs.
"U.S. Appl. No. 13/619,190, Response filed Sep. 1, 2015 to Final Office Action dated May 12, 2015", 30 pgs.
"U.S. Appl. No. 13/619,190, Response filed Sep. 1, 2016 to Final Office Action dated Mar. 1, 2016", 29 pgs.
"U.S. Appl. No. 13/619,190, Response filed Oct. 27, 2014 to Final Office Action dated Jun. 25, 2014", 13 pgs.
"U.S. Appl. No. 13/619,190, Response filed Nov. 18, 2013 to Restriction requirement mailed Oct. 18, 2013", 7 pgs.
"U.S. Appl. No. 13/619,190, Restriction Requirement dated Oct. 18, 2013", 7 pgs.
"U.S. Appl. No. 13/619,190, Supplemental Preliminary Amendment filed Apr. 15, 2013", 8 pgs.
"U.S. Appl. No. 13/944,441, Final Office Action dated Sep. 17, 2015", 7 pgs.
"U.S. Appl. No. 13/944,441, Non Final Office Action dated Apr. 20, 2015", 12 pgs.
"U.S. Appl. No. 13/944,441, Notice of Allowance dated Oct. 14, 2015", 8 pgs.
"U.S. Appl. No. 13/944,441, Preliminary Amendment filed Jul. 19, 2013", 8 pgs.
"U.S. Appl. No. 13/944,441, Response filed Mar. 30, 2015 to Restriction Requirement dated Feb. 2, 2015", 8 pgs.
"U.S. Appl. No. 13/944,441, Response filed Aug. 20, 2015 to Non Final Office Action dated Apr. 20, 2015", 16 pgs.
"U.S. Appl. No. 13/944,441, Response filed Oct. 5, 2015 to Final Office Action dated Sep. 17, 2015", 8 pgs.
"U.S. Appl. No. 13/944,441, Restriction Requirement dated Feb. 2, 2015", 6 pgs.
"U.S. Appl. No. 14/085,040, Final Office Action dated Nov. 12, 2015", 14 pgs.
"U.S. Appl. No. 14/085,040, Non Final Office Action dated Mar. 28, 2016", 10 pgs.
"U.S. Appl. No. 14/085,040, Non Final Office Action dated Jul. 21, 2015", 12 pgs.
"U.S. Appl. No. 14/085,040, Notice of Allowance dated Aug. 31, 2016", 6 pgs.
"U.S. Appl. No. 14/085,040, Response filed Mar. 7, 2016 to Final Office Action dated Nov. 12, 2015", 7 pgs.
"U.S. Appl. No. 14/085,040, Response filed Jun. 22, 2015 to Restriction Requirement dated Apr. 22, 2015", 8 pgs.
"U.S. Appl. No. 14/085,040, Response filed Jul. 28, 206 to Non Final Office Action dated Mar. 28, 2016", 11 pgs.
"U.S. Appl. No. 14/085,040, Response filed Oct. 21, 2015 to Non Final Office Action dated Jul. 21, 15", 34 pgs.
"U.S. Appl. No. 14/085,040, Restriction Requirement dated Apr. 22, 2015", 6 pgs.
"U.S. Appl. No. 14/226,051, Final Office Action dated Nov. 6, 2015", 10 pgs.
"U.S. Appl. No. 14/226,051, Non Final Office Action dated Apr. 3, 2015", 16 pgs.
"U.S. Appl. No. 14/266,051, Response filed Aug. 13, 2015 to Non Final Office Action dated Apr. 3, 2015", 11 pgs.
"U.S. Appl. No. 14/278,916, Appeal Brief filed Aug. 18, 2017", 77 pgs.
"U.S. Appl. No. 14/278,916, Appeal Decision dated Jan. 2, 2020", 13 pgs.
"U.S. Appl. No. 14/278,916, Examiner's Answer dated Oct. 3, 2017", 13 pgs.
"U.S. Appl. No. 14/278,916, Final Office Action dated Sep. 26, 2016", 11 pgs.
"U.S. Appl. No. 14/278,916, Non Final Office Action dated Apr. 4, 2017", 15 pgs.
"U.S. Appl. No. 14/278,916, Non Final Office Action dated May 11, 2015", 9 pgs.
"U.S. Appl. No. 14/278,916, Non Final Office Action dated May 25, 2016", 13 pgs.
"U.S. Appl. No. 14/278,916, Non Final Office Action dated Dec. 9, 2015", 10 pgs.
"U.S. Appl. No. 14/278,916, Notice of Allowance dated Mar. 2, 2020", 7 pgs.
"U.S. Appl. No. 14/278,916, Preliminary Amendment filed Jul. 9, 2014", 4 pgs.
"U.S. Appl. No. 14/278,916, Reply Brief filed Nov. 28, 2017", 17 pgs.
"U.S. Appl. No. 14/278,916, Response filed Mar. 22, 2017 to Final Office Action dated Sep. 26, 2016", 37 pgs.
"U.S. Appl. No. 14/278,916, Response filed May 9, 2016 to Final Office Action dated Dec. 9, 2015", 14 pgs.
"U.S. Appl. No. 14/278,916, Response filed Sep. 10, 2015 to Non Final Office Action dated May 11, 2015", 11 pgs.
"U.S. Appl. No. 14/278,916, Supplemental Notice of Allowability dated Apr. 22, 2020", 4 pgs.
"U.S. Appl. No. 14/278,916, Supplemental Preliminary Amendment filed Jul. 18, 2014", 7 pgs.
"U.S. Appl. No. 14/558,024, Examiner Interview Summary dated Dec. 21, 2016", 3 pgs.
"U.S. Appl. No. 14/558,024, Final Office Action dated Sep. 1, 2016", 15 pgs.
"U.S. Appl. No. 14/558,024, Non Final Office Action dated Jan. 15, 2016", 12 pgs.
"U.S. Appl. No. 14/558,024, Notice of Allowance dated Feb. 15, 2017", 11 pgs.

(56) References Cited

OTHER PUBLICATIONS

"U.S. Appl. No. 14/558,024, Notice of Allowance dated Apr. 24, 2017", 8 pgs.
"U.S. Appl. No. 14/558,024, Response filed Jun. 14, 2016 to Non Final Office Action dated Jan. 15, 2016", 11 pgs.
"U.S. Appl. No. 14/558,024, Response filed Dec. 30, 2016 to Final Office Action dated Sep. 1, 2016", 10 pgs.
"U.S. Appl. No. 14/722,701, Advisory Action dated Nov. 9, 2016", 3 pgs.
"U.S. Appl. No. 14/722,701, Final Office Action dated Sep. 15, 2016", 12 pgs.
"U.S. Appl. No. 14/722,701, Non Final Office Action dated May 6, 2016", 18 pgs.
"U.S. Appl. No. 14/722,701, Non Final Office Action dated Dec. 1, 2016", 8 pgs.
"U.S. Appl. No. 14/722,701, Notice of Allowance dated Mar. 22, 2017", 9 pgs.
"U.S. Appl. No. 14/722,701, Preliminary Amendment filed Jun. 16, 2015", 9 pgs.
"U.S. Appl. No. 14/722,701, PTO Response to Rule 312 Communication dated May 24, 2017", 2 pgs.
"U.S. Appl. No. 14/722,701, Response filed Feb. 24, 2017 to Non-Final Office Action dated Dec. 1, 2016", 12 pgs.
"U.S. Appl. No. 14/722,701, Response filed Aug. 3, 2016 to Non Final Office Action dated May 6, 2016", 15 pgs.
"U.S. Appl. No. 14/722,701, Response filed Oct. 31, 2016 to Final Office Action dated Sep. 15, 2016", 14 pgs.
"U.S. Appl. No. 14/722,701, Response filed Nov. 11, 2016 to Final Office Action dated Sep. 15, 2016", 14 pgs.
"U.S. Appl. No. 14/936,929, Advisory Action dated Jun. 23, 2017", 3 pgs.
"U.S. Appl. No. 14/936,929, Final Office Action dated May 23, 2017", 13 pgs.
"U.S. Appl. No. 14/936,929, Non Final Office Action dated Feb. 15, 2017", 12 pgs.
"U.S. Appl. No. 14/936,929, Non Final Office Action dated Jul. 26, 2017", 12 pgs.
"U.S. Appl. No. 14/936,929, Notice of Allowance dated Oct. 25, 2017", 9 pgs.
"U.S. Appl. No. 14/936,929, Preliminary Amendment filed Nov. 11, 2015", 7 pgs.
"U.S. Appl. No. 14/936,929, Response filed Jan. 20, 2017 to Restriction Requirement dated Dec. 14, 2016", 7 pgs.
"U.S. Appl. No. 14/936,929, Response filed May 4, 2017 to Non Final Office Action dated Feb. 15, 2017", 9 pgs.
"U.S. Appl. No. 14/936,929, Response filed Jun. 14, 2017 to Final Office Action dated May 23, 2017", 9 pgs.
"U.S. Appl. No. 14/936,929, Response filed Sep. 18, 2017 to Non Final Office Action dated Jul. 26, 2017", 10 pgs.
"U.S. Appl. No. 14/936,929, Restriction Requirement dated Dec. 14, 2016", 6 pgs.
"U.S. Appl. No. 15/285,689, Non Final Office Action dated Mar. 9, 2018", 10 pgs.
"U.S. Appl. No. 15/285,689, Notice of Allowability dated Jul. 27, 2018", 2 pgs.
"U.S. Appl. No. 15/285,689, Notice of Allowance dated Jul. 18, 2018", 6 pgs.
"U.S. Appl. No. 15/285,689, Preliminary Amendment filed Oct. 6, 2016", 12 pgs.
"U.S. Appl. No. 15/285,689, PTO Response to Rule 312 Communication dated Aug. 9, 2018", 2 pgs.
"U.S. Appl. No. 15/285,689, Response filed Jan. 29, 2018 to Restriction Requirement dated Dec. 11, 2017", 12 pgs.
"U.S. Appl. No. 15/285,689, Response filed Apr. 18, 2018 to Non Final Office Action dated Mar. 9, 2018", 17 pgs.
"U.S. Appl. No. 15/285,689, Restriction Requirement dated Dec. 11, 2017", 6 pgs.
"U.S. Appl. No. 15/285,689, Supplemental Preliminary Amendment filed May 10, 2017", 10 pgs.
"U.S. Appl. No. 15/629,794, Examiner Interview Summary dated Jul. 20, 2018", 3 pgs.
"U.S. Appl. No. 15/629,794, Final Office Action dated Apr. 19, 18", 19 pgs.
"U.S. Appl. No. 15/629,794, Non Final Office Action dated Nov. 3, 2017", 15 pgs.
"U.S. Appl. No. 15/629,794, Notice of Allowance dated Sep. 19, 2018", 14 pgs.
"U.S. Appl. No. 15/629,794, Response filed Mar. 2, 2018 to Non Final Office Action dated Nov. 3, 2017", 15 pgs.
"U.S. Appl. No. 15/629,794, Response filed Jul. 19, 2018 to Final Office Action dated Apr. 19, 2018", 10 pgs.
"U.S. Appl. No. 15/839,363, Preliminary Amendment filed Dec. 14, 2017", 9 pgs.
"U.S. Appl. No. 15/839,363, Restriction Requirement dated Apr. 24, 2019", 6 pgs.
"U.S. Appl. No. 15/926,794, Preliminary Amendment filed Jun. 26, 2017", 8 pgs.
"U.S. Appl. No. 15/978,686, Final Office Action dated Mar. 23, 2020", 6 pgs.
"U.S. Appl. No. 15/978,686, Non Final Office Action dated Dec. 19, 2019", 12 pgs.
"U.S. Appl. No. 15/978,686, Notice of Allowance dated Jun. 16, 2020", 6 pgs.
"U.S. Appl. No. 15/978,686, Preliminary Amendment filed Jun. 29, 2018", 6 pgs.
"U.S. Appl. No. 15/978,686, Response filed Mar. 9, 2020 to Non Final Office Action dated Dec. 19, 2019", 19 pgs.
"U.S. Appl. No. 15/978,686, Response filed May 20, 2020 to Final Office Action dated Mar. 23, 2020", 12 pgs.
"U.S. Appl. No. 15/978,686, Supplemental Preliminary Amendment filed Jul. 5, 2018", 9 pgs.
"U.S. Appl. No. 16/122,540, Non Final Office Action dated May 21, 2020", 9 pgs.
"U.S. Appl. No. 16/122,540, Notice of Allowance dated Sep. 22, 2020", 7 pgs.
"U.S. Appl. No. 16/122,540, Preliminary Amendment filed Sep. 12, 2018", 11 pgs.
"U.S. Appl. No. 16/122,540, Response filed May 4, 2020 to Restriction Requirement dated Mar. 2, 2020", 11 pgs.
"U.S. Appl. No. 16/122,540, Response filed Aug. 17, 2020 to Non Final Office Action dated May 21, 2020", 13 pgs.
"U.S. Appl. No. 16/122,540, Restriction Requirement dated Mar. 2, 2020", 6 pgs.
"U.S. Appl. No. 16/475,215, Examiner Interview Summary dated Feb. 23, 2021", 3 pgs.
"U.S. Appl. No. 16/475,215, Non Final Office Action dated Dec. 24, 2020", 19 pgs.
"U.S. Appl. No. 16/475,215, Notice of Allowance dated Apr. 21, 2021", 11 pgs.
"U.S. Appl. No. 16/475,215, Response filed Mar. 24, 2021 to Non Final Office Action dated Dec. 24, 2020", 13 pgs.
"U.S. Appl. No. 16/475,215, Response filed Dec. 1, 2020 to Restriction Requirement dated Nov. 13, 2020", 10 pgs.
"U.S. Appl. No. 16/475,215, Restriction Requirement dated Nov. 13, 2020", 7 pgs.
"U.S. Appl. No. 29/379,094, Application filed Nov. 15, 2010", 6 pgs.
"U.S. Appl. No. 29/379,094, Notice of Allowance dated Feb. 28, 2013", 12 pgs.
"U.S. Appl. No. 29/379,094, Response filed Nov. 21, 2012 to Restriction Requirement dated Oct. 23, 2012", 4 pgs.
"U.S. Appl. No. 29/379,094, Restriction Requirement dated Oct. 23, 2012", 7 pgs.
"Australian Application No. 2004203348, Office Action dated Jan. 13, 2010", 3 pgs.
"Australian Application Serial No. 2015355366, First Examination Report dated May 31, 2019", 3 pgs.
"Australian Application Serial No. 2018210296, First Examination Report dated Sep. 17, 2019", 3 pgs.
"Australian Application Serial No. 2018210296, Response filed Mar. 17, 2020 to First Examination Report dated Sep. 17, 2019", 17 pgs.

(56) References Cited

OTHER PUBLICATIONS

"Canadian Application No. 2,473,633, Office Action dated Mar. 12, 2010", 3 pgs.
"Canadian Application Serial No. 2,969,745, Office Action dated Aug. 19, 2019", 6 pgs.
"Canadian Application Serial No. 2,969,745, Office Action dated Nov. 28, 2019", 6 pgs.
"Canadian Application Serial No. 2,969,745, Response filed Mar. 26, 2020 to Office Action dated Nov. 28, 2019", 3 pgs.
"Canadian Application Serial No. 2,969,745, Response filed Nov. 19, 2019 to Office Action dated Aug. 19, 2019", 16 pgs.
"Canadian Application Serial No. 3,051,099, Office Action dated Oct. 5, 2020", 3 pgs.
"Canadian Application Serial No. 3,051,099, Response filed Feb. 15, 2021 to Office Action dated Oct. 5, 2020", 13 pgs.
"Chinese Application Serial No. 201580071660.1, Decision of Rejection dated Aug. 19, 2019", w/ English Transaltion, 18 pgs.
"Chinese Application Serial No. 201580071660.1, Office Action dated Mar. 14, 2019", W/English Translation, 15 pgs.
"Chinese Application Serial No. 201580071660.1, Office Action dated Jul. 3, 2018", w/English translation, 24 pgs.
"Chinese Application Serial No. 201580071660.1, Response filed May 14, 209 to Office Action dated Mar. 14, 2019", w/ English claims, 12 pgs.
"Chinese Application Serial No. 201580071660.1, Response filed Nov. 9, 2018 to Office Action dated Jul. 3, 2018", w/ English claims, 12 pgs.
"Chinese Application Serial No. 201880007640.1, Office Action dated Oct. 30, 2020", (W/English Translation), 20 pgs.
"Chinese Application Serial No. 201880007640.1, Response filed Feb. 26, 2021 to Office Action dated Oct. 30, 2020", (W/ English Claims), 12 pgs.
"European Application No. 04254352.0, European Search Report dated Jun. 22, 2005", 3 pgs.
"European Application Serial No. 04254352,0, Communication Pursuant to Article 94(3) EPC dated Nov. 11, 2019", 3 pgs.
"European Application Serial No. 04254352.0, Examination Notification Art. 94(3) dated Mar. 10, 2014", 5 pgs.
"European Application Serial No. 04254352.0, Examination Notification Art. 94(3) dated Apr. 22, 2013", 5 pgs.
"European Application Serial No. 04254352.0, Response filed Mar. 24, 20 to Communication Pursuant to Article 94(3) EPC dated Nov. 11, 2019", 16 pgs.
"European Application Serial No. 04254352.0, Response filed Sep. 2, 2013 to Examination Notification Art. 94(3) dated Apr. 22, 2013", 10 pgs.
"European Application Serial No. 13715785.5, Decision to Grant dated Feb. 4, 2016", 2 pgs.
"European Application Serial No. 13715785.5, Office Action dated Sep. 7, 2015", 26 pgs.
"European Application Serial No. 13715785.5, Response filed May 27, 2015 to Communication pursuant to Rules 161(2) and 162 EPC dated Nov. 20, 2014", 22 pgs.
"European Application Serial No. 15808304.8, Response filed Feb. 20, 2018 to Action dated Aug. 10, 2018", 13 pgs.
"European Application Serial No. 18742374.4, Extended European Search Report dated Nov. 10, 2020", 3 pgs.
"European Application Serial No. 18742374.4, Response to Communication pursuant to Rules 161(2) and 162 EPC filed Mar. 20, 2020", 10 pgs.
"Forbes Magazine Ranks Zimmer Holdings Among the 'Best Managed Companies in America'", PR Newswire, (Jan. 23, 2004), 2 pgs.
"International Application Serial No. PCT/US2013/029251, International Preliminary Report on Patentability dated Sep. 18, 2014", 9 pgs.
"International Application Serial No. PCT/US2013/029251, International Search Report dated Jun. 19, 2013", 5 pgs.
"International Application Serial No. PCT/US2013/029251, Written Opinion dated Jun. 19, 2013", 7 pgs.
"International Application Serial No. PCT/US2015/022471, International Preliminary Report on Patentability dated Oct. 6, 2016", 10 pgs.
"international Application Serial No. PCT/US2015/022471, International Search Report dated Jul. 28, 2015", 5 pgs.
"International Application Serial No. PCT/US2015/022471, Written Opinion dated Jul. 28, 2015", 8 pgs.
"International Application Serial No. PCT/US2015/062070, International Preliminary Report on Patentability dated Jun. 15, 2017", 9 pgs.
"International Application Serial No. PCT/US2015/062070, International Search Report dated Feb. 12, 2016", 4 pgs.
"International Application Serial No. PCT/US2015/062070, Written Opinion dated Feb. 12, 2016", 7 pgs.
"International Application Serial No. PCT/US2018/013795, International Preliminary Report on Patentability dated Aug. 1, 2019", 9 pgs.
"International Application Serial No. PCT/US2018/013795, International Search Report dated Mar. 12, 2018", 2 pgs.
"International Application Serial No. PCT/US2018/013795, Written Opinion dated Mar. 12, 2018", 7 pgs.
"Japanese Application No. 2004-216179, Office Action dated May 26, 2009", (W/ English Translation), 8 pgs.
"Japanese Application Serial No. 2017-529340, Final Notification of Reasons for Refusal dated Jun. 9, 2020", with English translation, 8 pages.
"Japanese Application Serial No. 2017-529340, Notification of Reasons for Refusal dated Nov. 15, 2019", with English translation, 9 pages.
"Japanese Application Serial No. 2017-529340, Response filed Jan. 14, 2020 to Notification of Reasons for Refusal dated Nov. 15, 2019", with English claims, 16 pages.
"Japanese Application Serial No. 2017-529340, Response filed Aug. 20, 2020 to Final Notification of Reasons for Refusal dated Jun. 9, 2020", w/ English claims, 18 pgs.
"Japanese Application Serial No. 2019-539802, Notification of Reasons for Refusal dated Oct. 20, 2020", w/ English Translation, 11 pgs.
"Japanese Application Serial No. 2019-539802, Response filed Jan. 19, 2021 to Notification of Reasons for Refusal dated Oct. 20, 2020", (W/ English Claims), 11 pgs.
"Orthopaedic Salvage System Femoral/Tibial Augmentation", Biomet Orthopedics, Inc., Product Brochure, (2003, 2004), 12 pgs.
"Zimmer Trabecular Metal Cone", Zimmer, Inc., (2004), 2 pgs.
Neer, Charles S., et al., "Glenoid Bone-Grafting in Total Shoulder Arthroplasty", The Journal of Bone and Joint Surgery, vol. 70-A, No. 8,, (Sep. 1998), pp. 1154-1162.
Walch, Gilles, et al., "Morphologic Study of the Glenoid in Primary Glenohumeral Osteoarthritis", The Journal of Arthroplasty, vol. 14, No. 6, (Sep. 1999), pp. 756-760.
"Canadian Application Serial No. 3,051,099, Office Action dated May 20, 2021", 4 pgs.
"U.S. Appl. No. 16/475,215, Corrected Notice of Allowability dated Jul. 23, 2021", 3 pgs.
"Chinese Application Serial No. 201880007640.1, Office Action dated Jun. 24, 2021", (W English Translation), 17 pgs.
"Chinese Application Serial No. 201880007640.1, Response filed Aug. 24, 2021 to Office Action dated Jun. 24, 2021", w English claims, 11 pgs.
"U.S. Appl. No. 16/475,215, Corrected Notice of Allowability dated Sep. 9, 2021", 3 pgs.
"Canadian Application Serial No. 3,051,099, Response filed Sep. 16, 2021 to Office Action dated May 20, 2021", 13 pgs.

\* cited by examiner

MODULAR AUGMENT COMPONENT

PRIORITY CLAIM

This application is a Divisional of U.S. patent application Ser. No. 16/475,215, tiled Jul. 1, 2019, which is a U.S. National Stage Filing under 35 U.S.C. 371 from International Patent Application Serial No. PCT/US2018/013795, filed Jan. 16, 2018, which published on Jul. 26, 2018 as WO 2018/0136393 A1, which application claims priority to U.S. Provisional Application No. 62/448,547, filed on Jan. 20, 2017, the contents of which are hereby incorporated by refence in their entireties.

FIELD OF THE DISCLOSURE

The present disclosure relates to surgical implant systems, including implants, instruments, and methods for installing an implant. Specifically, the present disclosure relates to systems and methods for securing a glenoid implant to a glenoid.

BACKGROUND

Surgical procedures for repairing or reconstructing a joint can require securely fastening a surgical implant to a bone. For example, shoulder joint reconstruction can require fixing a glenoid implant to a scapula to reproduce or replicate a glenoid cavity on the scapula. The surgical implant can be securely fastened to the bone in a variety of ways, including mechanical fasteners and adhesive. SUMMARY To better illustrate the system disclosed herein, a non-limiting list of examples is provided here:

Example 1 is a central augment for use in a shoulder replacement procedure, the central augment comprising: a body including a glenoid engagement surface shaped to interface with a central portion of a reamed glenoid and a second surface opposite the first curved surface and defining a recess sized to receive a boss of a glenoid component; a protrusion extending from the second surface within the recess, the protrusion sized to be received within a bore defined by the boss of the glenoid component; and a post extending from the glenoid engagement surface, the post sized to be received in a bore formed in the central portion of the glenoid, wherein at least one of the body and the post includes a porous metal coating.

In Example 2, the subject matter of Example 1 optionally includes wherein the first curved surface has a bulbous shape.

In Example 3, the subject matter of any one or more of Examples 1-2 optionally include wherein the first curved surface has a spherical shape.

In Example 4, the subject matter of any one or more of Examples 1-3 optionally include wherein the first curved surface is shaped for a specific patient.

In Example 5, the subject matter of any one or more of Examples 1-4 optionally include wherein the post includes a threaded portion.

In Example 6, the subject matter of any one or more of Examples 1-5 optionally include wherein the post includes a barbed portion.

In Example 7, the subject matter of any one or more of Examples 1-6 optionally include wherein the post is a fluted peg.

In Example 8, the subject matter of any one or more of Examples 1-7 optionally include wherein the recess includes a tapered profile complementary to the portion of the glenoid component.

In Example 9, the subject matter of any one or more of Examples 1-8 optionally include wherein the protrusion includes one or more external threads configured to mate with one or more internal threads disposed within the boss of the glenoid component.

In Example 10, the subject matter of any one or more of Examples 1-9 optionally include wherein at least one of the body and the post includes a porous metal coating.

Example 11 is a modular glenoid system for use in a shoulder replacement procedure, the modular glenoid system comprising: a glenoid component including an articulation surface, a glenoid engaging surface opposite the articulation surface, and a boss extending from the glenoid engaging surface; and a modular augment including: a first outer surface, a second internal surface opposite the first outer surface and defining a recess sized to receive the boss, a post, the first outer surface forming a dome and shaped to interface with a reamed portion of a glenoid, the post extending from the first outer surface and sized to be received in a bore created in the glenoid; and a protrusion extending from the second internal surface and sized to be received within a bore in the boss.

In Example 12, the subject matter of Example 11 optionally includes wherein the protrusion includes a male threaded portion and the bore includes a female threaded portion for receiving the male threaded portion.

In Example 13, the subject matter of any one or more of Examples 11-12 optionally include wherein the glenoid component includes a plurality of pegs spaced about the boss.

In Example 14, the subject matter of any one or more of Examples 11-13 optionally include wherein the modular augment is selected from a plurality of modular augments, each of the plurality of modular augments sized to complement a different sized central defect.

Example 15 is a method for replacing a glenoid component, the method comprising: reaming a central portion of a glenoid; implanting a modular augment into the central portion of the glenoid, the modular augment including a first curved surface, a second curved surface opposite the first curved surface and defining a recess sized to receive a boss extending from an augment engaging surface of a glenoid component, the first curved surface including a post extending therefrom sized to be received in a bore created in the boss of the glenoid component; and implanting the glenoid component into the glenoid, the glenoid component coupled to the modular augment via the post and the bore created in the boss.

In Example 16, the subject matter of Example 15 optionally includes selecting the modular augment from a plurality of modular augments, each of the plurality of modular augments sized to complement a different sized central defect.

In Example 17, the subject matter of any one or more of Examples 15-16 optionally include wherein the modular augment is patient specific.

In Example 18, the subject matter of any one or more of Examples 15-17 optionally include wherein implanting the modular augment and the glenoid component occur simultaneously.

In Example 19, the subject matter of Example 18 optionally includes screwing the post into the bore of the boss of the glenoid component.

In Example 20, the subject matter of any one or more of Examples 15-19 optionally include wherein the modular augment is press fitted with the glenoid component.

In Example 21, the modular augment or modular glenoid system of any one of or any combination of Examples 1-20 is optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Through injury, trauma, aging, or other degenerative conditions a joint, such as the shoulder, can become damaged or otherwise less mobile. In addition, the injury, trauma, aging, or other condition can cause repeated injury. For example, an injury to a shoulder can cause a central defect or other damage to a glenoid socket. The central defect or other damage can cause the humeral head to more easily become dislocated from the glenoid socket. For instance, a person can suffer from a glenoid chondral defect that can lead to or be caused by glenohumeral dislocation.

As disclosed herein, a modular augment can be used to repair a central defect. The modular augment can include a body and a post that extends from the body. The post and body portions can be implanted into a central portion of a glenoid socket to assist in repairing a central defect. Addressing a central defect with the modular augment can allow for existing bone around a central portion of the glenoid to be saved or otherwise remain undisturbed during a surgical procedure.

The central defect can be in any bony anatomy. For example, the central defect can be in a shoulder joint, a hip joint, or the hand or wrist. For instance, in a shoulder joint the central defect can be in the glenoid. In a hip joint the central defect can be in an acetabular fossa. In a hand, the central defect can be in a base of a metacarpal bone or phalanges bones.

Figure 1:
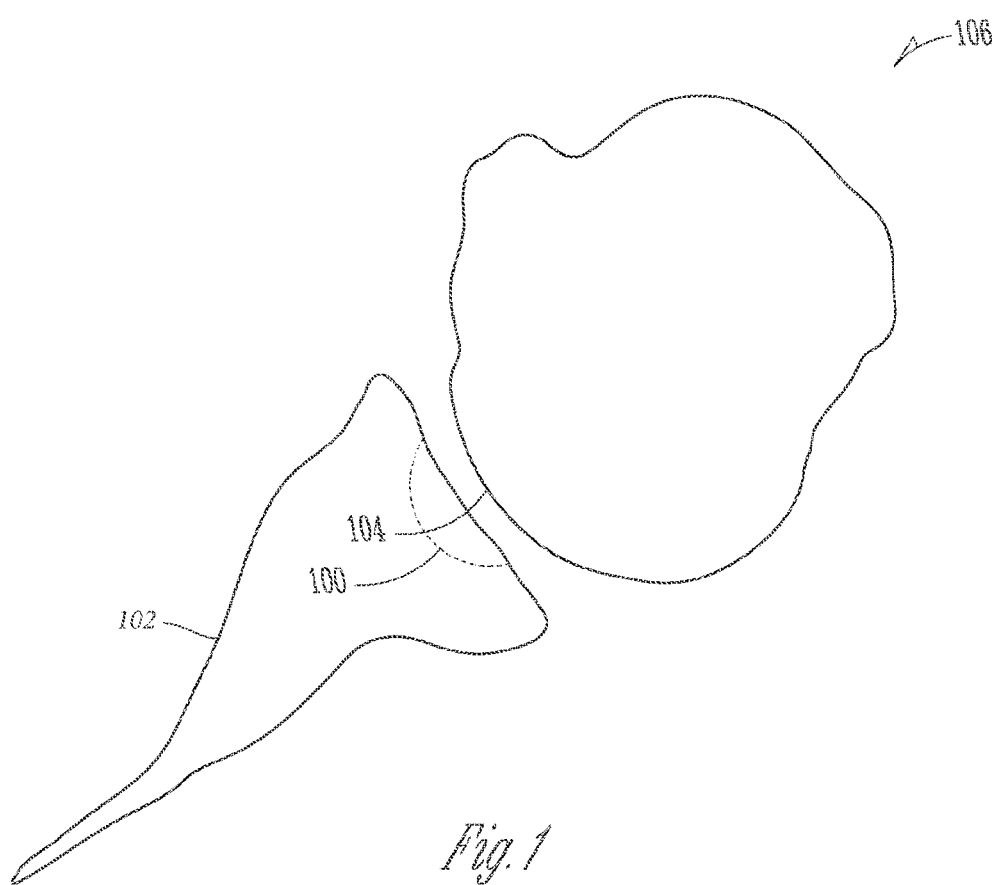
FIG. 1 shows a central defect in a glenoid.

FIG. 1 shows a central defect 100 in a bone 102. The bone 102 can be a glenoid, acetabular fossa, etc. The central defect 100 can be a bare spot or other central area of cartilage loss on a fossa (such as a glenoid fossa) with or without underlying bone damage. Other types of central defects can include, but are not limited to, cartilage lesions of the glenehumeral joint such as Hill-Sachs lesions or articular cartilage lesions. As shown in FIG. 1, the central defect 100 can affect the way a bone surface 104 (such as a humeral surface) of a head portion 106 (such as a humeral head) interacts with the bone 102.

Figure 2:
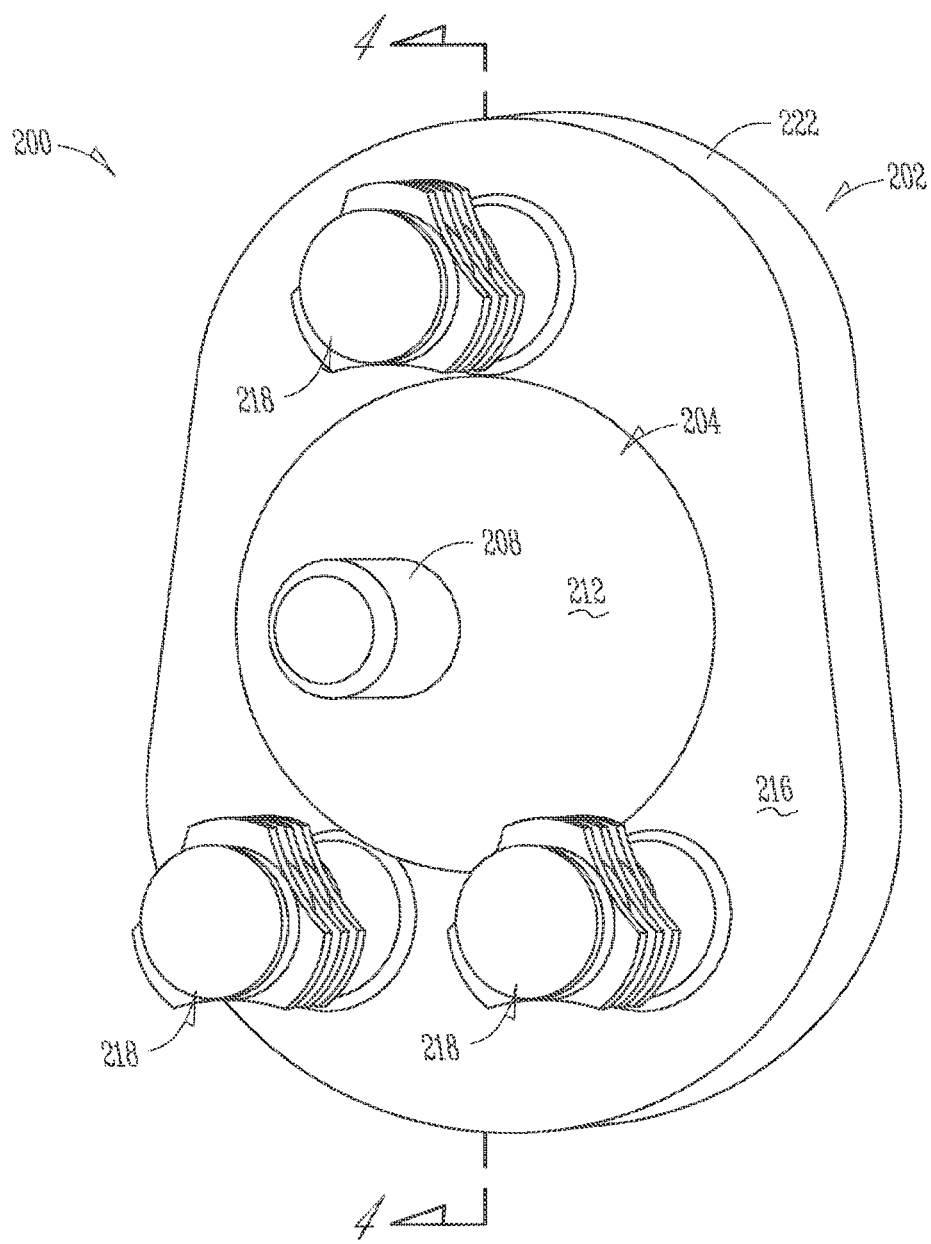
FIG. 2 shows a perspective view of a modular glenoid system in accordance with at least one example of the present disclosure.
Figure 3:
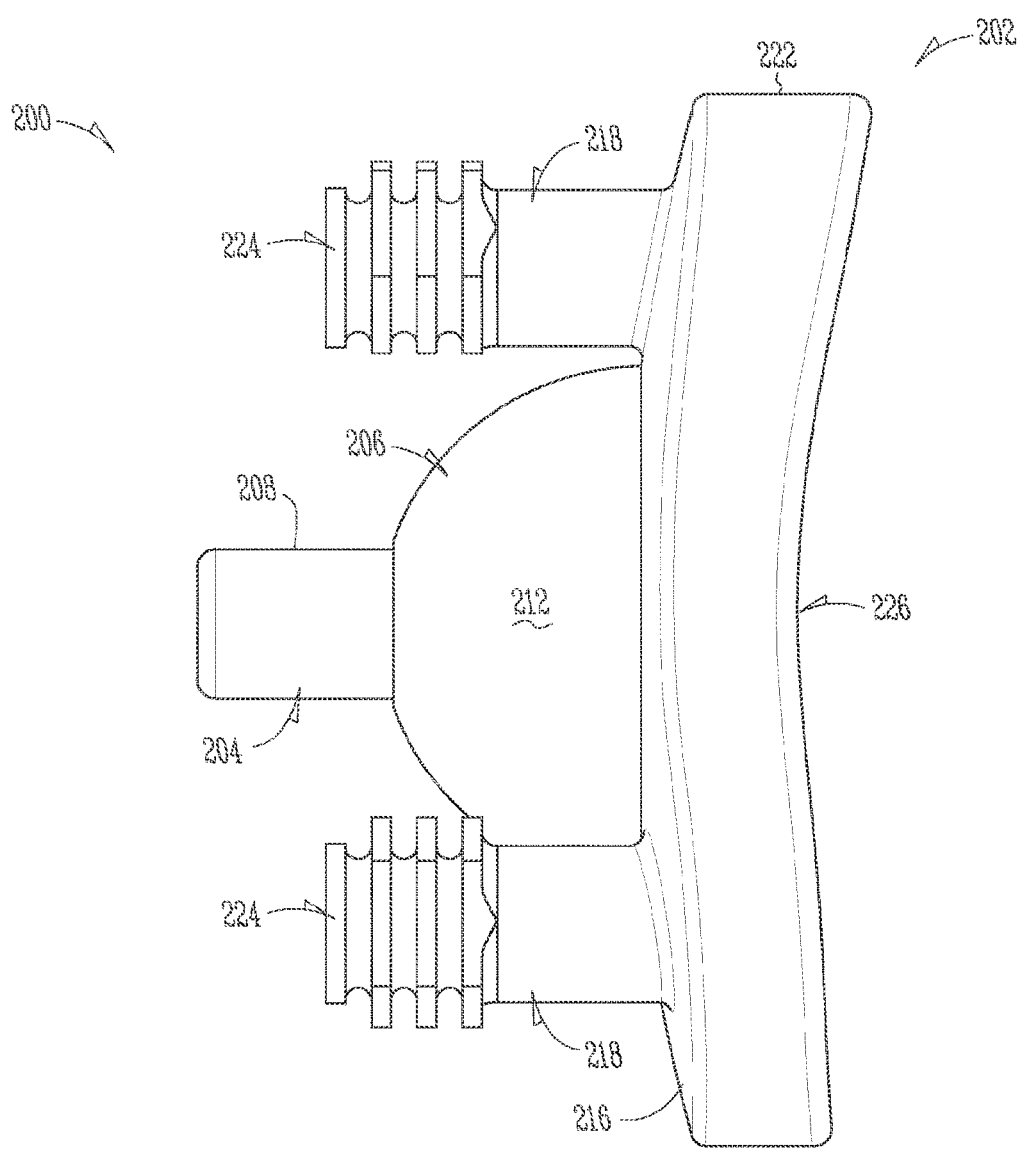
FIG. 3 shows a side view of a modular glenoid system in accordance with at least one example of the present disclosure.
Figure 4:
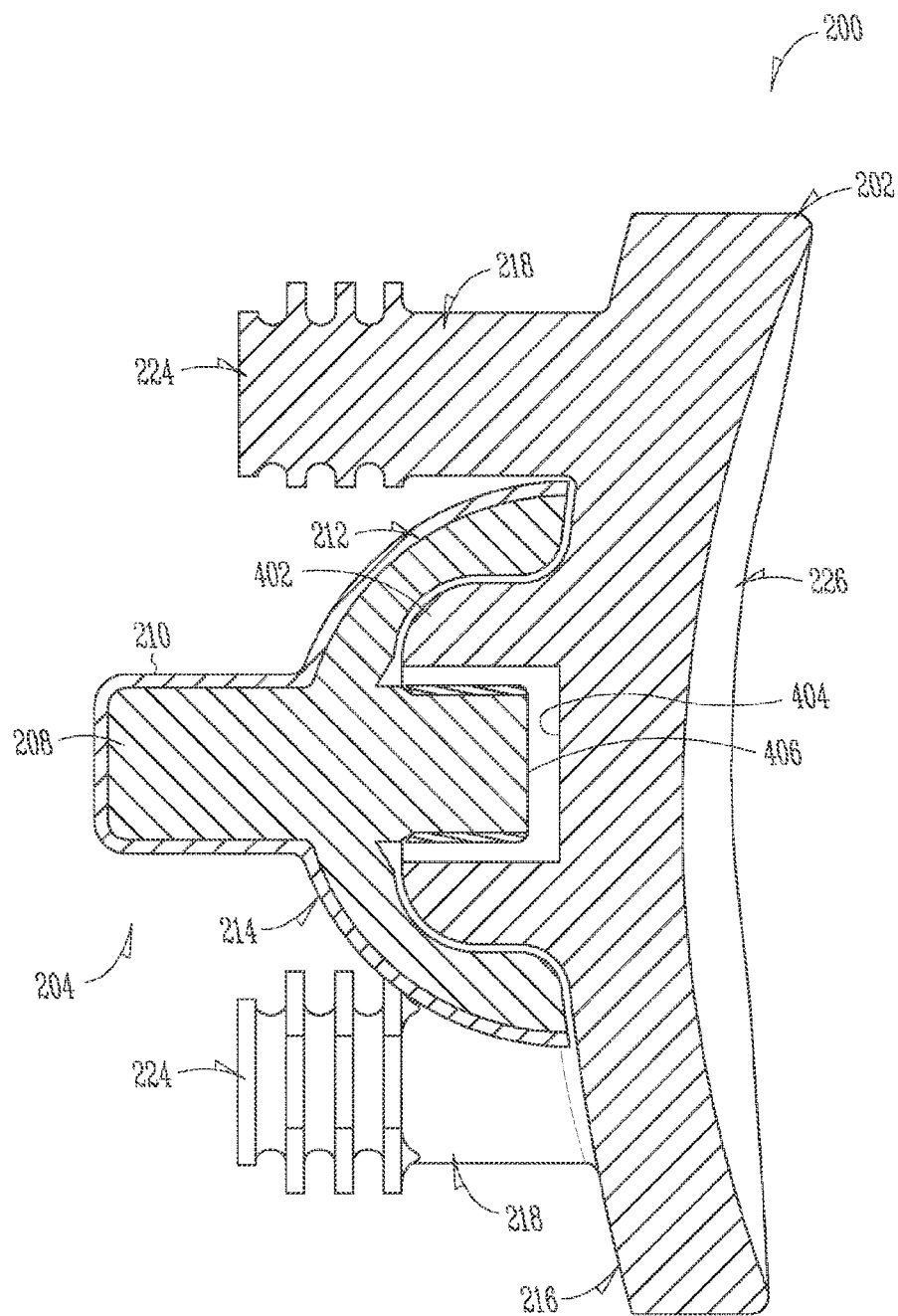
FIG. 4 shows a section view of a modular glenoid system in accordance with at least one example of the present disclosure.

With reference to FIGS. 2-4, a modular glenoid system 200 in accordance with some aspects of the present disclosure is illustrated. The modular glenoid system 200 can include a glenoid component 202 and a modular augment 204. As disclosed herein, the modular augment 204 can be inserted into a glenoid (such as bone 102), with minimal resecting of the glenoid. For example, a central portion of the glenoid can be reamed or otherwise prepared to receive the modular augment 204 while the infraglenoid tubercle or other portions of the glenoid cavity or scapular can remain in a natural or otherwise undisturbed state. While FIGS. 2-4 show a system described with respect to a glenoid and in an anatomical configuration, the systems and methods disclosed herein can be apply in reverse procedures such as a revers shoulder arthroplasty, in other joints such as the hip joint, etc.

The modular augment 204 can include a body 206 and a post 208 that extends from the body 206. As shown in FIG. 4, the body 206 and the post 208 can include a porous metal layer 210 on at least a portion thereof. In addition, and in various examples, only the post 208 can include the porous metal layer 210. Furthermore, and in various examples, only the body 206 can include the porous metal layer 210. Moreover, in various examples, the post 208 and/or the body 206 can be formed as a porous component instead of having a porous layer formed thereon.

The porous metal layer 210 (or porous components) can allow for bone ingrowth to further secure the modular augment 204 to the glenoid. The porous metal layer 210 can be a highly porous, three-dimensional metallic structure that can incorporate one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing bony tissue or other tissue to grow into the porous structure over time to enhance fixation (e.g., osseointegration) between the structure and surrounding bodily structures. In accordance with examples disclosed herein, an open porous metal structure, or a portion thereof, can have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal® Technology available from Zimmer, Inc., of Warsaw, Ind. Trabecular Metal® is a trademark of Zimmer, Inc. Such a material can be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure can be fabricated using a selective laser sintering (SLS) or other additive manufacturing-type process such as direct metal laser sintering or electron beam melting. In one example, a three-dimensional porous article can be produced in layer-wise fashion from a laser-fusible powder, e.g., a single-component metal powder, which can be deposited one layer at a time. The powder can be fused, remelted or sintered, by the application of laser energy that is directed to portions of the powder layer corresponding to a cross section of the article. After the fusing of the powder in each layer, an additional layer of powder can be deposited, and a further fusing step can be carried out, with fused portions or lateral layers fusing so as to fuse portions of previous laid layers until a three-dimensional article is complete. In certain examples, a laser can selectively fuse powdered material by scanning cross-sections generated from a 3-D digital description of the article, e.g., from a CAD file or scan data, on the surface of a powder bed. Complex geometries can be created using such techniques, and in some instances, net shape and near net shape implants can be constructed. In some examples, a non-porous or essentially non-porous base substrate can provide a foundation upon which a three-dimensional porous structure can be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate can be in direct contact with the ligaments of the highly porous structure, for example, approximately 15%, 20%, or 25%, of the surface area of the substrate can be in direct contact with the ligaments of the highly porous structure.

A highly porous, three-dimensional metallic structure can be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure can be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure can have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrowth within the open porous metal. In some instances, a highly porous, three-dimensional metallic structure, once formed, can be infiltrated and coated with one or more coating materials such as biocompatible metals such as any of those disclosed herein.

In addition to a porous metal, the post 208 or the porous metal layer 210 can form threads, barbs, or other protrusions that can allow the modular augment 204 to be screwed into or otherwise secured to the glenoid. Furthermore, the post 208 can be tapered and can include one or more flutes, fins, ribs, or other projections extending therefrom. The threads, barbs, flutes, fins, ribs, or other protrusions can provide surfaces for bone contact and can create anchoring structures to help secure the modular augment 204. For instance, during recovery, bone can grow in between the threads, barbs, flutes, fins, ribs, or other protrusions to assist in securing the module augment 204 to the glenoid.

The body 206 can include a curved surface 212 and a glenoid component engaging surface 214. The curved surface 212 can match a profile of a reamed portion of the glenoid. For example, a reamer can have a hemispherical profile or other bulbous shape that corresponds to a hemispherical or bulbous shape of the curved surface 212. In addition, the curved surface 212 can be patient specific. For instance, a surgeon can use images of a patient's glenoid and specify a shape of the curved surface 212 to match the anatomy of the patient. The modular augment 204 can then be manufactured with the curved surface 212 matched to the specific contours (reamed or natural) for a particular patient.

The glenoid component engaging surface 214 can match a profile of the glenoid component 202. For example, the glenoid component 202 can include a boss 402 that projects from a glenoid engaging surface 216. Stated another way, the glenoid component engaging surface 214 can define a recess sized to receive a portion of the glenoid component 202 (e.g., the boss 402) or, as shown in FIG. 4, an entirety of the glenoid component 202 (e.g., the boss 402), and extend around the glenoid component 202 in a dome-like manner. The boss 402 can be centrally located as shown in FIG. 2 or offset as needed for a patient. The glenoid component engaging surface 214 can allow the modular augment 204 to engage the glenoid component 202 via any suitable connection, such as a threaded connection, a snap fit connection, or a press fit connection. The boss 402 can define a bore 404 that can receive a protrusion 406 that extends from the glenoid component engaging surface 214. The curved surface 212 can form a dome-like structure and encapsulate the protrusion 406 such that the protrusion 406 extends towards a base of the dome-like structure away from a top of the dome-like structure. In an example, the protrusion 406 can include one or more external threads configured to engage one or more internal threads formed within the bore 404. In addition, the glenoid component engaging surface 214 and the curved surface 212 can create a thin walled structure that can allow the body 206 to be flexible. As a result, body 206 can stretch to accommodate bosses of differing sizes. Furthermore, the glenoid component engaging surface 214 can form a recess that includes a tapered profile complementary to a portion of the glenoid component 204 (e.g., the boss 402).

By having the modular augment 204 and the glenoid component 202 as separate components of the modular glenoid system 200, the glenoid component 202 can be adjusted or replaced without disturbing the modular augment 204. For example, after the modular glenoid system 200 is implanted, a revision might be needed at a later date. Because of the modular nature of the glenoid system 200, the glenoid component 202 can be removed without removing the modular augment 204.

In addition, the modular augment 204 can be utilized with glenoid components 202 of varying size and configurations. For example, the modular augment 204 and the glenoid component 202 can be components of a system that includes a plurality of modular augments and glenoid components. During a surgical procedure, a surgeon can select a modular augment 204 that best conforms to a size, shape, or other aspect of a central defect. The protrusion 406 and the glenoid component engaging surface 214 of the various modular augments can be a standard size and boss 402 and bore 404 of the various glenoid components can be a standard size such that modular augments and glenoid components can be mixed and matched to create an implant more tailored to a patient.

For example, the central defect of a patient can be small. Thus, a surgeon can select a modular augment 204 that is of similar size and shape of the central defect. By being able to select an appropriately sized modular augment 204, the amount of bone needed to be removed during a reaming process or other disturbance to the glenoid can be minimized. This can improve healing times as well as minimize patient pain and discomfort.

The modular augment 204 can be made of polymers, ceramics, metallic materials, or any combination thereof. For example, modular augment 204 can be injection molded from a polymer, such as a vitamin E stabilized polymer and coated with the porous metal layer 210 as indicated above. In addition, the porous metal layer 210 can coat only the post 208, the curved surface 212, or any portions thereof.

The modular augment 204 can be manufactured using any number of manufacturing techniques or a combination of techniques. For example, the body 206 can be an injection molded polymer that can attach to a metallic portion that forms the post 208 and the protrusion 406, which can be machined from a billet material.

The glenoid component 202 can include one or more pegs 218. The pegs 218 can extend from the glenoid engaging surface 216. For example, the pegs 218 can extend from the glenoid engaging surface 216 such that one or more of the pegs 218 is parallel to the post 208. In addition, one or more of the pegs 218 can extend from the glenoid engaging surface 216 such that one or more of the pegs 218 is not parallel to the post 208.

The pegs 218 can be monolithic to the glenoid component 202 or separate components that can be removably coupled to the glenoid component 202. For example, a body 222 of the glenoid component 202 can include one or more holes that can receive the pegs 218. The pegs 218 can be threaded, press fit, snap fit, etc. into the one or more holes. In addition, the body 222 of the glenoid component 202 and the pegs 218 can be formed of a continuous material (i.e., monolithic). For example, the body 222 and the pegs 218 can be formed from a polymer and during a single operation such as injection or direct compression molding.

The pegs 218 can be spaced about the modular augment 204 in any configuration, and any number of pegs 218 can be provided. As shown in FIG. 2, the pegs 218 can be arranged in a triangular pattern such as isosceles, equilateral, scalene, or otherwise. In addition to triangular patterns, the pegs 218 can be arranged in square or rectangular patterns when there are four or more pegs.

The pegs 218 can include fins or flutes 224. The number of flutes 224 can vary between pegs. For instance, one peg can have three flutes and another peg can have two flutes. The pegs 218 and flutes 225 can be made of or coated with a porous metal as disclosed herein. The pegs 218 can all be the same length, or one of the pegs 218 can have a length that is different from at least one other peg 218.

The glenoid component 202 can include an articulation surface 226. The articulation surface 226 can allow a humeral head (natural bone or prosthetic) to articulate and allow for a range of motion of a humerus. The contour of the articulation surface 226 can be patient-specific. For example, a surgeon can use images of a patient's glenoid to specify a shape and contour of the glenoid component 202 and the articulation surface 226. The glenoid component can then be manufactured with the articulation surface 226 tailored to a patient.

As disclosed herein, the glenoid component 202 can be selected from a plurality of glenoid components during a surgical procedure. For example, once a patient's glenoid and humeral head are exposed, a surgeon can examine the glenoid and humeral head and select a glenoid component from one of the plurality of glenoid components that most closely matches a geometry of the patient's glenoid. For instance, the surgeon can select a glenoid component that has a glenoid articulating surface with a curvature similar to that of the patient.

Figure 5:
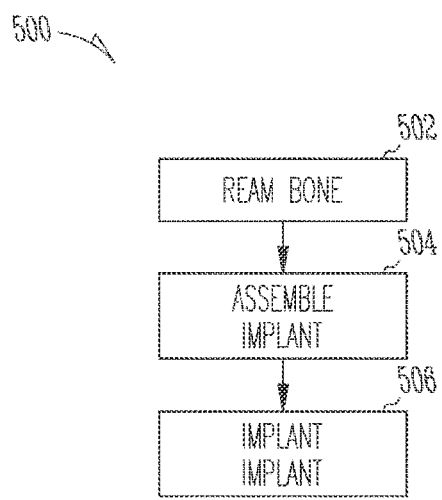
FIG. 5 shows an example method for a glenoid arthroplasty in accordance with at least one example of the present disclosure.

FIG. 5 shows a flowchart for a method 500 for glenoid arthroplasty in accordance with at least one example disclosed herein. The method 500 begins at stage 502 where a bone can be reamed. For example, as disclosed herein, a central portion of a glenoid can be reamed. During the reaming process, bone surrounding the central portion of the glenoid can remain unreamed. For example, one or both of the supraglenoid tubercle or the infraglenoid tubercle can remain undisturbed during the reaming process thereby preserving natural bone. As indicated herein, the reamer used in the reaming process can match a shape of the curved surface of the modular augment. In addition, reaming the bone can include drilling a hole in the glenoid for the post and/or pegs. For instance, the reamer can include a pilot bit that can drill a hole in the glenoid to accept the peg. Alternatively, the surgeon can drill a pilot hole and holes for the pegs as needed.

From stage 502, the method 500 can proceed to stage 504 where the modular augment can be assembled. In an example, prior to implantation, the modular augment providing the best anatomical fit can be selected from a plurality of modular augments having different sizes, shapes, dimensions, or the like. The glenoid component can be press fitted to the modular augment or screwed into the modular augment as disclosed herein.

From stage 504, the method 500 can proceed to stage 506 where the assembled implant can be implanted. As disclosed herein, the modular augment can be press fit, snap fit, screwed, or otherwise fastened to the reamed portion of the glenoid. During implantation, the post of the modular augment can be inserted into the glenoid to anchor the modular augment to the glenoid. Implanting the glenoid component can include securing the glenoid component to the modular augment. In addition, the various pegs of the glenoid component can be embedded into the glenoid during the implanting process.

Alternatively, the modular augment and the glenoid component can be implanted independently of one another. For example, the modular implant can be implanted prior to implanting the glenoid component. Once the modular augment is implanted the glenoid component can be implanted and attached to both the glenoid and the modular augment.

The modular augment and the glenoid component can be patient-specific or part of an implantation system. For example, during the surgical procedure, the surgeon can select the modular augment, the glenoid component, or both, from a plurality of modular augments and a plurality of glenoid components based on observations and measurements of the patient's glenoid during surgery.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A method for implanting a glenoid component, the method comprising:
    reaming a central portion of a glenoid;
    providing the glenoid component;
    providing a central augment comprising a body including a glenoid engagement surface having a continuous hemispherical shape sized and configured to interface with the central portion of the reamed glenoid and a second curved surface opposite the glenoid engagement surface defining a recess sized and shaped to receive a boss of the glenoid component; a protrusion extending from the second curved surface within the recess, the protrusion including an externally threaded surface operable to be received within an internally threaded bore formed within the boss of the glenoid component; and a post extending from the glenoid engagement surface, the post sized to be received in a bore formed in the central portion of the glenoid, wherein the body, the protrusion, and the post are monolithic;
    implanting the central augment into the central portion of the glenoid; and
    implanting the glenoid component into the glenoid, the glenoid component coupled to the central augment via the protrusion and the internally threaded bore formed in the boss.

2. The method of claim 1, further comprising selecting the central augment from a plurality of central augments, each of the plurality of central augments sized to complement a different sized central defect.

3. The method of claim 1, wherein the central augment is patient specific.

4. The method of claim 1, wherein implanting the central augment and the glenoid component occur simultaneously.

5. The method of claim 4, further comprising screwing the post into the bore of the boss of the glenoid component.

6. The method of claim 1, wherein the central augment is press fitted with the glenoid component.

7. The method of claim 1, further comprising drilling a pilot hole while reaming the central portion of the glenoid.

8. A method for replacing a glenoid component, the method comprising:
    reaming a central portion of a glenoid;
    providing the glenoid component comprising an articulation surface, a glenoid engaging surface opposite the articulation surface, and a boss extending from the glenoid engaging surface, the boss defining a bore having an internal thread;
    providing a monolithic modular augment comprising a first outer surface having a continuous hemispherical shape, a second internal surface opposite the first outer surface and defining a recess sized to receive the boss, and a post, the first outer surface forming a dome and shaped to interface with a reamed portion of a glenoid, the post extending from the first outer surface and sized to be received in a bore created in the glenoid, and a protrusion extending from the second internal surface and having an externally thread sized to be received within the bore and engage the internal thread of the boss;
    implanting the monolithic modular augment into the central portion of the glenoid; and
    implanting the glenoid component into the glenoid, the glenoid component coupled to the monolithic modular augment via the protrusion and the internally threaded bore formed in the boss.

9. The method of claim 8, further comprising selecting the monolithic modular augment from a plurality of monolithic modular augments, each of the plurality of monolithic modular augments sized to complement a different sized central defect.

10. The method of claim 8, further comprising selecting the glenoid component from a plurality of glenoid components, each of the plurality of glenoid components sized to complement a different sized glenoid.

11. The method of claim 8, further comprising assembling the monolithic modular augment and the glenoid component so that implanting the modular augment and the glenoid component occur simultaneously.

12. The method of claim 11, wherein assembling the monolithic modular augment and the glenoid component comprises screwing the post into the bore of the boss.

13. The method of claim 11, wherein assembling the monolithic modular augment and the glenoid component comprises press fitting the post into the bore of the boss.

14. The method of claim 8, further comprising drilling a pilot hole while reaming the central portion of the glenoid using a reamer with a pilot bit.

15. The method of claim 8, further comprising:
    selecting the monolithic modular augment from a plurality of monolithic modular augments, each of the plurality of monolithic modular augments sized to complement a different sized central defect; and
    selecting the glenoid component from a plurality of glenoid components, each of the plurality of glenoid components sized to complement a different sized glenoid.

16. A method for replacing a glenoid component, the method comprising:
    reaming a central portion of a glenoid;
    providing the glenoid component;
    providing a central augment comprising a body including a glenoid engagement surface having a continuous hemispherical shape sized and configured to interface with the central portion of the reamed glenoid and a second curved surface opposite the glenoid engagement surface defining a recess sized and shaped to receive a boss of the glenoid component; a protrusion extending from the second curved surface within the recess, the protrusion including an externally threaded surface operable to be received within an internally threaded bore formed within the boss of the glenoid component; and a post extending from the glenoid engagement surface, the post sized to be received in a bore formed in the central portion of the glenoid, wherein the body, the protrusion, and the post are monolithic;

assembling the central augment and the glenoid component to form a single component; and implanting the central augment into the central portion of the glenoid and the glenoid component into the glenoid.

17. The method of claim 16, wherein assembling the central augment and the glenoid component includes press fitting the post into the bore of the boss.

18. The method of claim 17, wherein assembling the central augment and the glenoid component includes screwing the post into the bore of the boss.

19. The method of claim 16, further comprising drilling a pilot hole prior to reaming the central portion of the glenoid.

20. The method of claim 16, further comprising drilling a pilot hole while reaming the central portion of the glenoid using a reamer with a pilot bit.

\* \* \* \* \*